United States Patent
Finigan et al.

(10) Patent No.: US 9,454,911 B2
(45) Date of Patent: Sep. 27, 2016

(54) FLIGHT CONTROL TEST SIMULATOR SYSTEM AND METHOD

(71) Applicant: The Boeing Company, Chicago, IL (US)

(72) Inventors: John S. Finigan, Edgewood, WA (US); James D. Edgerton, Renton, WA (US); Gregory J. Hughes, Seattle, WA (US)

(73) Assignee: The Boeing Company, Chicago, IL (US)

( * ) Notice: Subject to any disclaimer, the term of this patent is extended or adjusted under 35 U.S.C. 154(b) by 271 days.

(21) Appl. No.: 14/447,582

(22) Filed: Jul. 30, 2014

(65) Prior Publication Data

US 2016/0035239 A1 Feb. 4, 2016

(51) Int. Cl.
*G01M 5/00* (2006.01)
*G01N 3/14* (2006.01)
*G09B 9/10* (2006.01)

(52) U.S. Cl.
CPC ............... *G09B 9/10* (2013.01); *G01M 5/005* (2013.01); *G01M 5/0016* (2013.01); *G01N 3/14* (2013.01); *G01N 2203/04* (2013.01)

(58) Field of Classification Search
CPC .... G01M 5/005; G01M 5/0016; G01N 3/08; G01N 2203/0019; G01N 2203/0021; G01N 2203/0246; G01N 2203/04; G01N 3/20; G01N 2203/0005; G01N 2203/0073
See application file for complete search history.

(56) References Cited

U.S. PATENT DOCUMENTS

| 2,319,675 | A | * | 5/1943 | Grinter | G01M 5/005 428/174 |
| 2,340,505 | A | * | 2/1944 | Beed | G01M 5/0016 73/798 |
| 4,453,413 | A | * | 6/1984 | Schneider | G01M 5/005 73/802 |
| 4,748,854 | A | * | 6/1988 | Rao | G01N 3/32 73/799 |
| 4,768,391 | A | * | 9/1988 | Hayes | G01M 99/007 73/865.9 |
| 6,530,272 | B2 | * | 3/2003 | Uchida | G01M 5/005 73/170.01 |
| 6,880,409 | B2 | * | 4/2005 | Kawabe | G01N 3/24 73/856 |
| 7,246,527 | B2 | * | 7/2007 | Ostgaard | G01N 3/04 73/159 |
| 7,380,463 | B2 | * | 6/2008 | Posada Escobar | G01N 3/24 73/788 |

(Continued)

*Primary Examiner* — David A Rogers

(57) ABSTRACT

There is provided a flight control test simulator system and method. The system has a flight control assembly with at least one actuator and with a flight controller configured to actuate the at least one actuator. The system further has an aerodynamic load simulator coupled to the flight control assembly and configured to adjustably induce a simulated continuous aerodynamic load on the flight control assembly. The aerodynamic load simulator has a continuously adjustable spring rate constant assembly configured to adjust the spring rate constant of the induced simulated continuous aerodynamic load over a range of predetermined flight profiles.

20 Claims, 13 Drawing Sheets

(56) References Cited

U.S. PATENT DOCUMENTS

| | | | |
|---|---|---|---|
| 7,421,906 B2* | 9/2008 | Saves-Saint-Germes | G01M 5/005 73/802 |
| 7,426,871 B2* | 9/2008 | Saves-Saint-Germes | G01M 5/005 73/802 |
| 7,672,817 B2* | 3/2010 | Marsh | G01C 11/025 703/2 |
| 7,677,096 B2* | 3/2010 | Robinson | B64F 5/0045 73/170.02 |
| 7,690,264 B2* | 4/2010 | Robinson | B64F 5/0045 73/812 |
| 8,082,802 B1* | 12/2011 | Sadegh | G01N 3/08 73/760 |
| 8,365,610 B2* | 2/2013 | Decraecker | 73/794 |
| 8,479,591 B2* | 7/2013 | Cerreta | B64F 5/0045 73/802 |
| 8,688,408 B2* | 4/2014 | Marsh | G01C 11/025 244/13 |
| 8,857,265 B2* | 10/2014 | Silva | G01N 3/04 73/788 |
| 9,354,134 B2* | 5/2016 | Commo | G01M 9/062 |
| 2004/0069072 A1* | 4/2004 | Kawabe | G01N 3/24 73/841 |
| 2006/0037402 A1* | 2/2006 | Musial | G01M 7/00 73/664 |
| 2006/0070457 A1* | 4/2006 | De Lair | B64F 5/0045 73/847 |
| 2006/0101921 A1* | 5/2006 | Ostgaard | G01N 3/04 73/804 |
| 2006/0144996 A1* | 7/2006 | Carl | B64C 5/10 244/99.2 |
| 2006/0156836 A1* | 7/2006 | Ny | G01R 31/2887 73/866.5 |
| 2007/0256504 A1* | 11/2007 | Robinson | B64F 5/0045 73/812 |
| 2008/0139374 A1* | 6/2008 | LeFeuvre | G01M 7/027 494/10 |
| 2008/0271523 A1* | 11/2008 | Marsh | G01C 11/025 73/118.03 |
| 2009/0056431 A1* | 3/2009 | Jones | G01M 17/04 73/118.03 |
| 2010/0212449 A1* | 8/2010 | Hill | A61B 5/1071 74/490.08 |
| 2013/0127103 A1* | 5/2013 | Hill | A61B 5/1071 269/58 |
| 2013/0174665 A1* | 7/2013 | Silva | G01N 3/04 73/788 |
| 2013/0313358 A1* | 11/2013 | Hale | B64C 13/28 244/99.3 |
| 2014/0013856 A1* | 1/2014 | Gunter | G01N 3/08 73/819 |
| 2015/0020603 A1* | 1/2015 | Kismarton | G01M 5/0091 73/800 |
| 2016/0035239 A1* | 2/2016 | Finigan | G09B 9/10 73/865.6 |
| 2016/0041050 A1* | 2/2016 | Vera | G01L 5/22 73/788 |

* cited by examiner

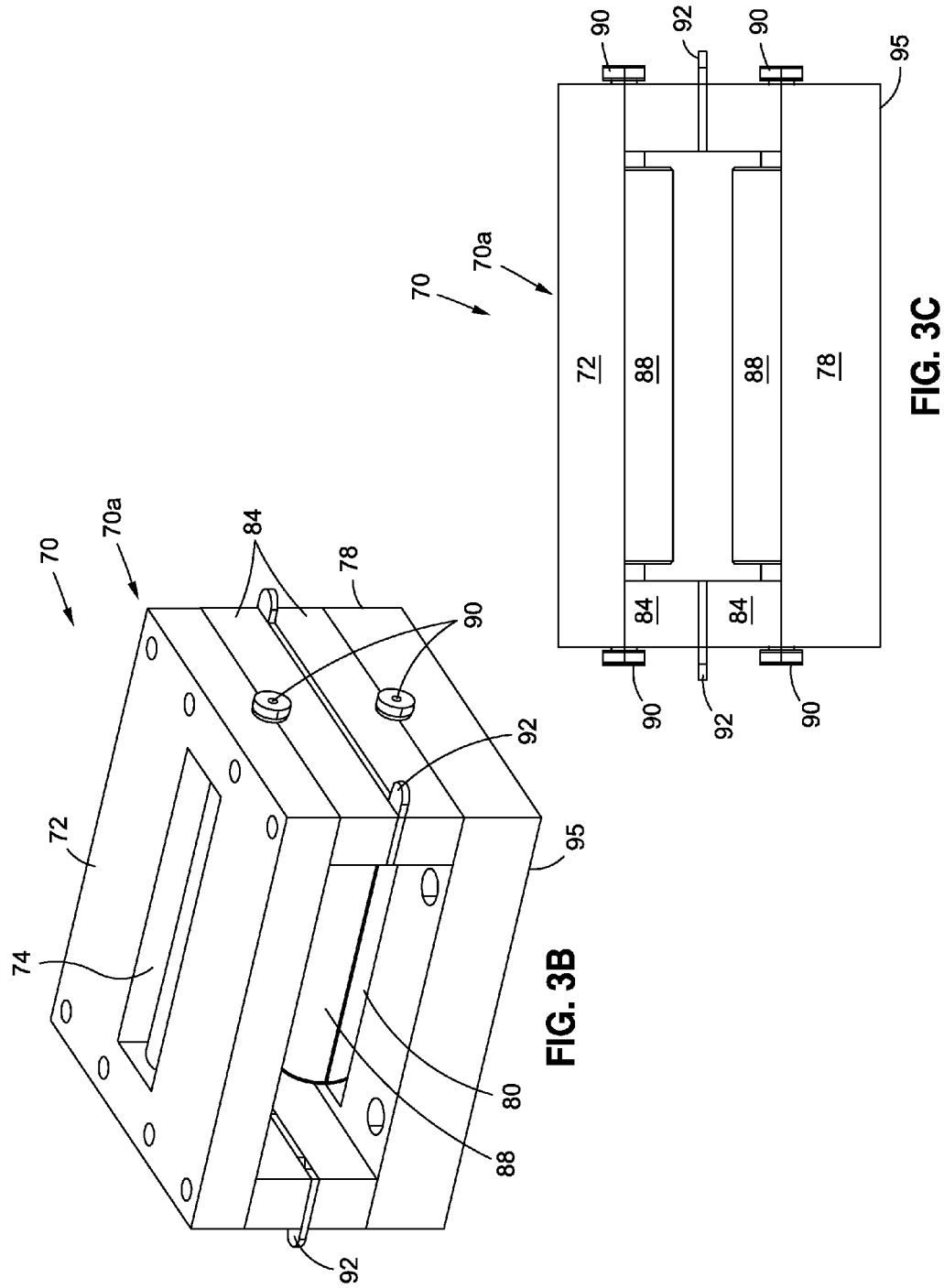

FLIGHT CONTROL TEST SIMULATOR SYSTEM AND METHOD

BACKGROUND

1) Field of the Disclosure

The disclosure relates generally to load testing systems and methods, and more particularly, to spring load testing systems and methods for performing flight control tests, such as flight control test simulations, on a flight control surface.

2) Description of Related Art

Mechanical testing and integrated systems testing of component parts, or of test specimens of component parts, are often performed in the manufacture of air vehicles, such as aircraft, rotorcraft, spacecraft, and other air vehicles. Such mechanical testing and integrated systems testing provide material property data, such as strength, hardness ductility, and other data about the material as tested under various conditions, such as compression, tension, load and temperature. In turn, such mechanical testing and integrated systems testing provide information relating to the suitability of a material for its intended application. Such information aids in the design of component parts that will perform as expected.

Known spring load systems and methods may be used for simulating aerodynamic loads on aircraft flight control surfaces and other mechanical systems or integrated systems in a test lab environment. However, existing flight control test simulator testing using such known spring load systems and methods may require that the testing be halted to make physical and/or geometric modifications to the spring load systems in order to change the aerodynamic load condition by modifying the effective spring rate. Such halting of the testing may result in increased test downtime and increased labor, tools, and costs to adjust the spring rates. In addition, existing flight control test simulator testing using such known spring load systems and methods may necessitate that test conditions be grouped in specific aerodynamic states which may complicate testing. Further, existing flight control test simulator testing using such known spring load systems and methods may prevent the execution of test scenarios where aerodynamic loads vary during a test run (i.e., airspeed changing during the test condition). Moreover, although existing flight control test simulator testing using such known spring load systems and methods provide repeatable loads with little or no hysteresis, they provide no automated system or method of adjusting or modifying the aerodynamic load condition and spring rate during test execution.

Accordingly, there is a need in the art for an improved flight control test simulator system and method that provide advantages over known systems and methods.

SUMMARY

This need for an improved flight control test simulator system and method is satisfied by this disclosure. As discussed in the below detailed description, embodiments of the improved flight control test simulator system and method may provide significant advantages over known systems and methods.

In one embodiment of the disclosure, there is provided a flight control test simulator system. The system comprises a flight control assembly having at least one actuator and having a flight controller configured to actuate the at least one actuator.

The system further comprises an aerodynamic load simulator coupled to the flight control assembly and configured to adjustably induce a simulated continuous aerodynamic load on the flight control assembly. The aerodynamic load simulator has a continuously adjustable spring rate constant assembly configured to adjust the spring rate constant of the induced simulated continuous aerodynamic load over a range of predetermined flight profiles.

In another embodiment of the disclosure, there is provided an aircraft flight control test simulator system for testing a simulated surface or a flight control surface. The aircraft flight control test simulator system is automated and comprises a flight control assembly having at least one actuator, having a flight controller configured to actuate the at least one actuator, and having the simulated surface or the flight control surface.

An aerodynamic load simulator is coupled to the flight control assembly and configured to adjustably induce a simulated continuous aerodynamic load on the flight control assembly. The aerodynamic load simulator comprises a continuously adjustable spring rate constant assembly configured to adjust the spring rate constant of the induced simulated continuous aerodynamic load over a range of predetermined flight profiles. The aerodynamic load simulator further comprises an input assembly configured to input a tensile load and a compressive load from the simulated surface or the flight control surface to the continuously adjustable spring rate constant assembly.

In another embodiment of the disclosure, there is provided a method for testing a simulated surface or a flight control surface. The method comprises the step of determining a flight profile for a flight control test. The method further comprises the step of coupling a flight control assembly to an aerodynamic load simulator.

The method further comprises the step of operating the flight control assembly over the flight profile. The method further comprises the step of inducing an aerodynamic load on the flight control assembly while operating the flight control assembly. The method further comprises the step of adjusting a spring rate constant for the aerodynamic load simulator during operation of the flight control assembly.

The features, functions, and advantages that have been discussed can be achieved independently in various embodiments of the disclosure or may be combined in yet other embodiments further details of which can be seen with reference to the following description and drawings.

BRIEF DESCRIPTION OF THE DRAWINGS

The disclosure can be better understood with reference to the following detailed description taken in conjunction with the accompanying drawings which illustrate preferred and exemplary embodiments, but which are not necessarily drawn to scale, wherein:

FIG. 3B is an illustration of an assembled front perspective view of the adjustable fulcrum assembly of FIG. 3A;

FIG. 3C is an illustration of an assembled front view of the adjustable fulcrum assembly of FIG. 3B;

DETAILED DESCRIPTION

Disclosed embodiments will now be described more fully hereinafter with reference to the accompanying drawings, in which some, but not all of the disclosed embodiments are shown. Indeed, several different embodiments may be provided and should not be construed as limited to the embodiments set forth herein. Rather, these embodiments are provided so that this disclosure will be thorough and will fully convey the scope of the disclosure to those skilled in the art.

Figure 1A:
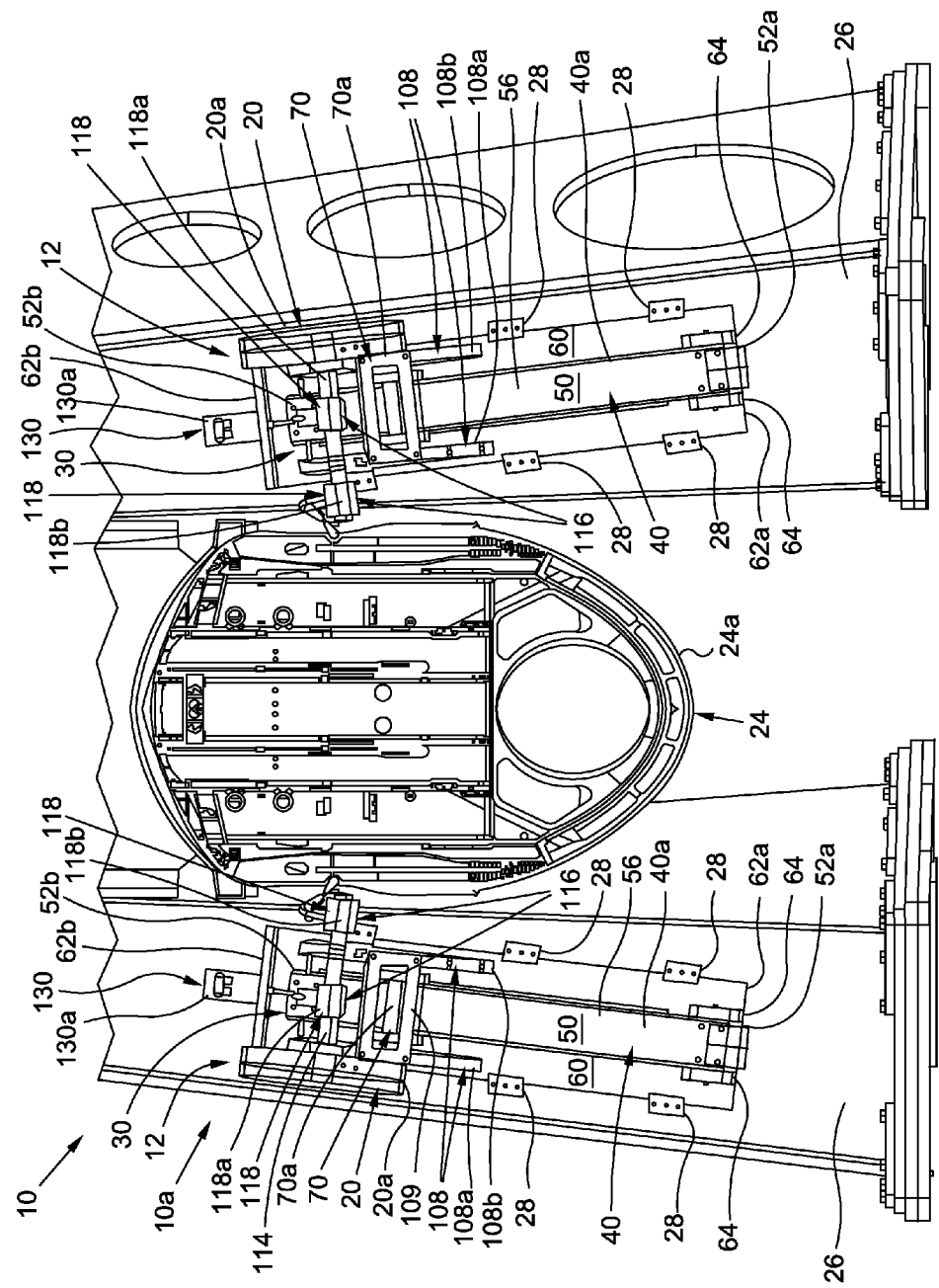
FIG. 1A is an illustration of a front perspective view of a flight control test simulator system of the disclosure.
Figure 5:
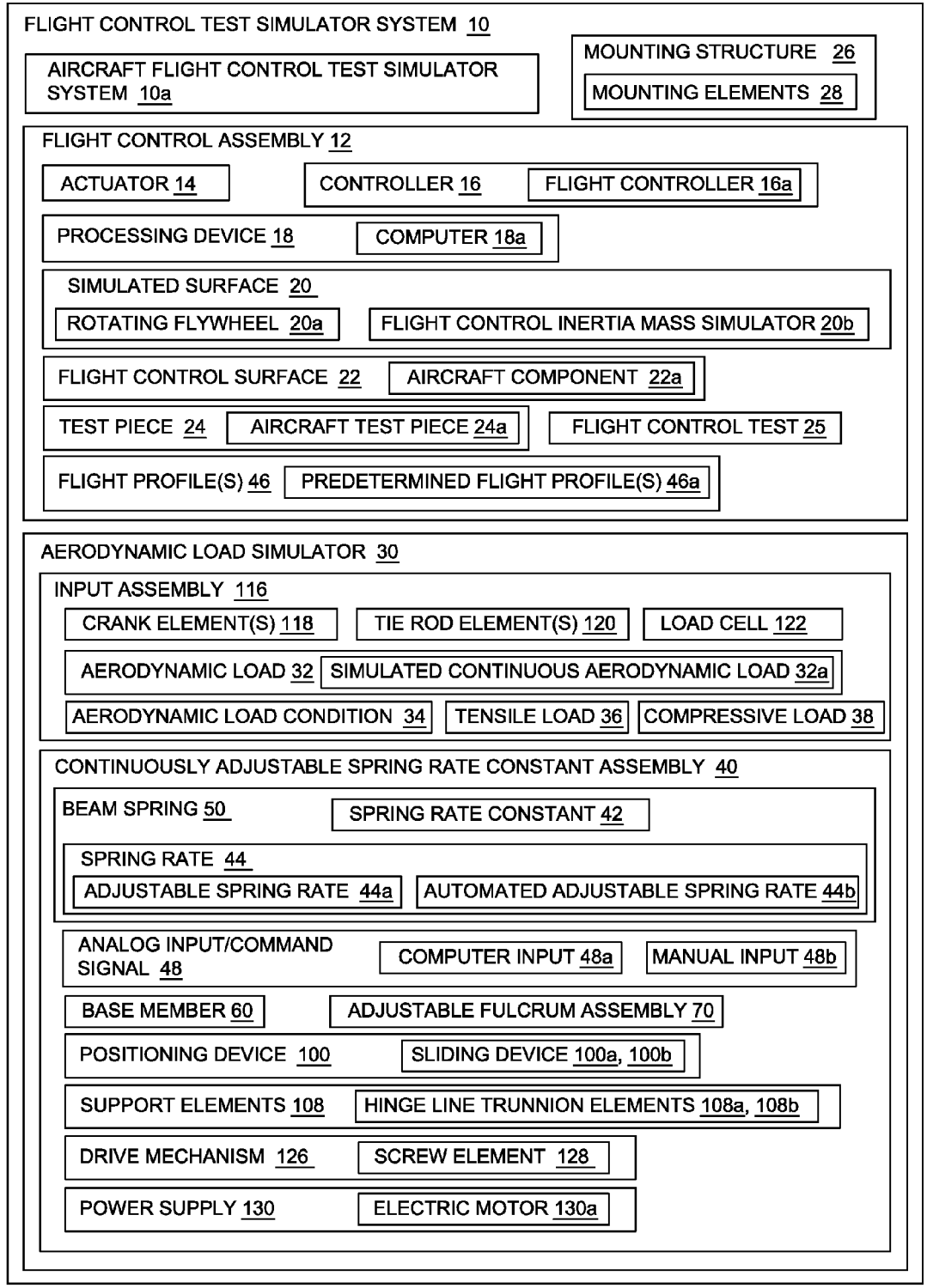
FIG. 5 is an illustration of a block diagram of an exemplary embodiment of a flight control test simulator system of the disclosure.

Now referring to the Figures, FIG. 1A is an illustration of a front perspective view of a flight control test simulator system 10 of the disclosure. In one embodiment of the disclosure, as shown in FIG. 1A, the flight control test simulator system 10 comprises an aircraft flight control test simulator system 10a. FIG. 5 is an illustration of a block diagram of an exemplary embodiment of the flight control test simulator system 10, such as in the form of aircraft flight control test simulator system 10a, of the disclosure.

As shown in FIG. 1A, the flight control test simulator system 10, such as in the form of aircraft flight control test simulator system 10a, comprises a flight control assembly 12. The flight control assembly 12 (see FIGS. 1A, 5) has at least one actuator 14 (see FIG. 5) and has a flight controller 16 (see FIG. 5) configured to actuate the at least one actuator 14. The controller 16 (see FIG. 5) is preferably a flight controller 16a (see FIG. 5).

The flight control assembly 12 (see FIGS. 1A, 5) may further comprise a processing device 18 (see FIG. 5), such as a computer 18a (see FIG. 5). The processing device 18 (see FIG. 5) may be used for processing software, such as aerodynamic conditions simulation software or other suitable software, and/or may be used for obtaining and processing test data from the flight control test 25 (see FIG. 5) performed by the flight control test simulator system 10 (see FIG. 5).

As shown in FIG. 1A, the flight control test simulator system 10 further comprises an aerodynamic load simulator 30 coupled to the flight control assembly 12. The aerodynamic load simulator 30 (see FIGS. 1A, 5) is preferably configured to adjustably induce a simulated continuous aerodynamic load 32a (see FIG. 5) on the flight control assembly 12 (see FIG. 5). The aerodynamic load simulator 30 (see FIGS. 1A, 5) includes a continuously adjustable spring rate constant assembly 40 (see FIGS. 1A, 5), such as in the form of a continuously adjustable spring rate constant assembly 40a (see FIGS. 1A, 1E), or in the form of a continuously adjustable spring rate constant assembly 40b (see FIG. 2A). The continuously adjustable spring rate constant assembly 40 (see FIGS. 1A, 5) is preferably configured to adjust a spring rate constant 42 (see FIG. 5) of the induced simulated continuous aerodynamic load 32a (see FIG. 5) over a range of predetermined flight profiles 46a (see FIG. 5).

Figure 1B:
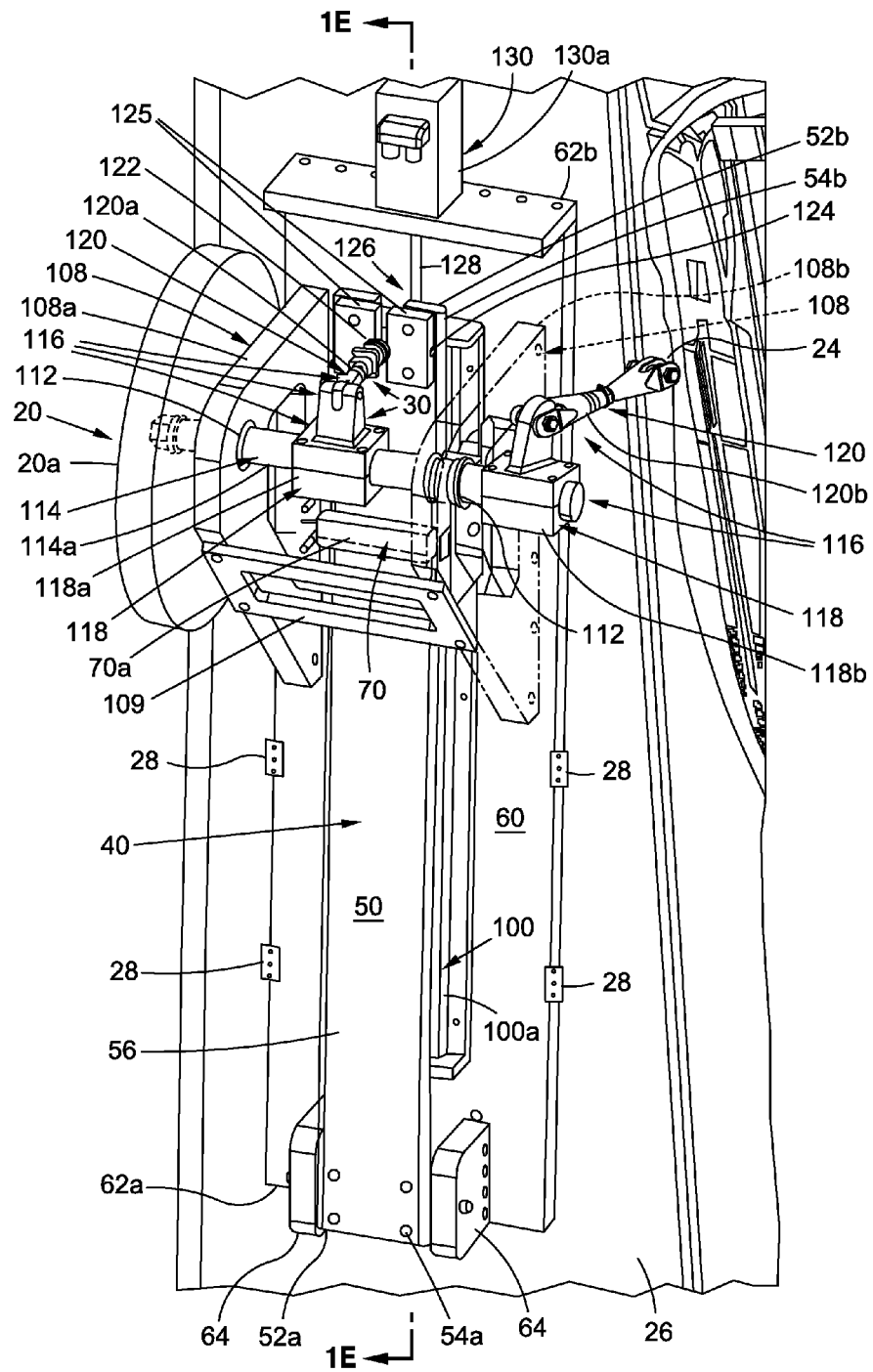
FIG. 1B is an illustration of a close-up front perspective view of an embodiment of an aerodynamic load simulator with a continuously adjustable spring rate constant assembly of the flight control test simulator system of FIG. 1A.
Figure 1C:
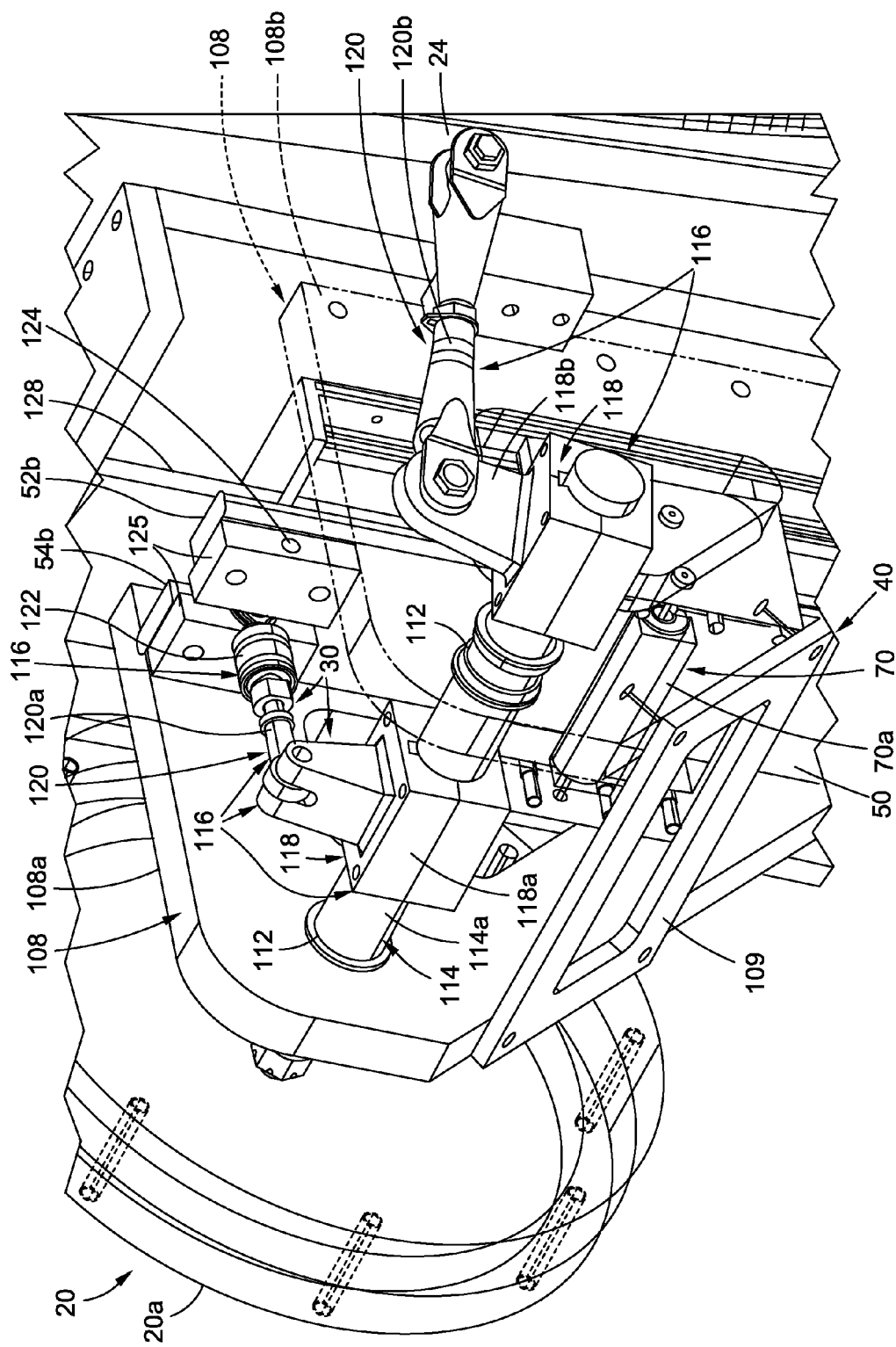
FIG. 1C is an illustration of a close-up side perspective view of the aerodynamic load simulator of FIG. 1B.
Figure 1D:
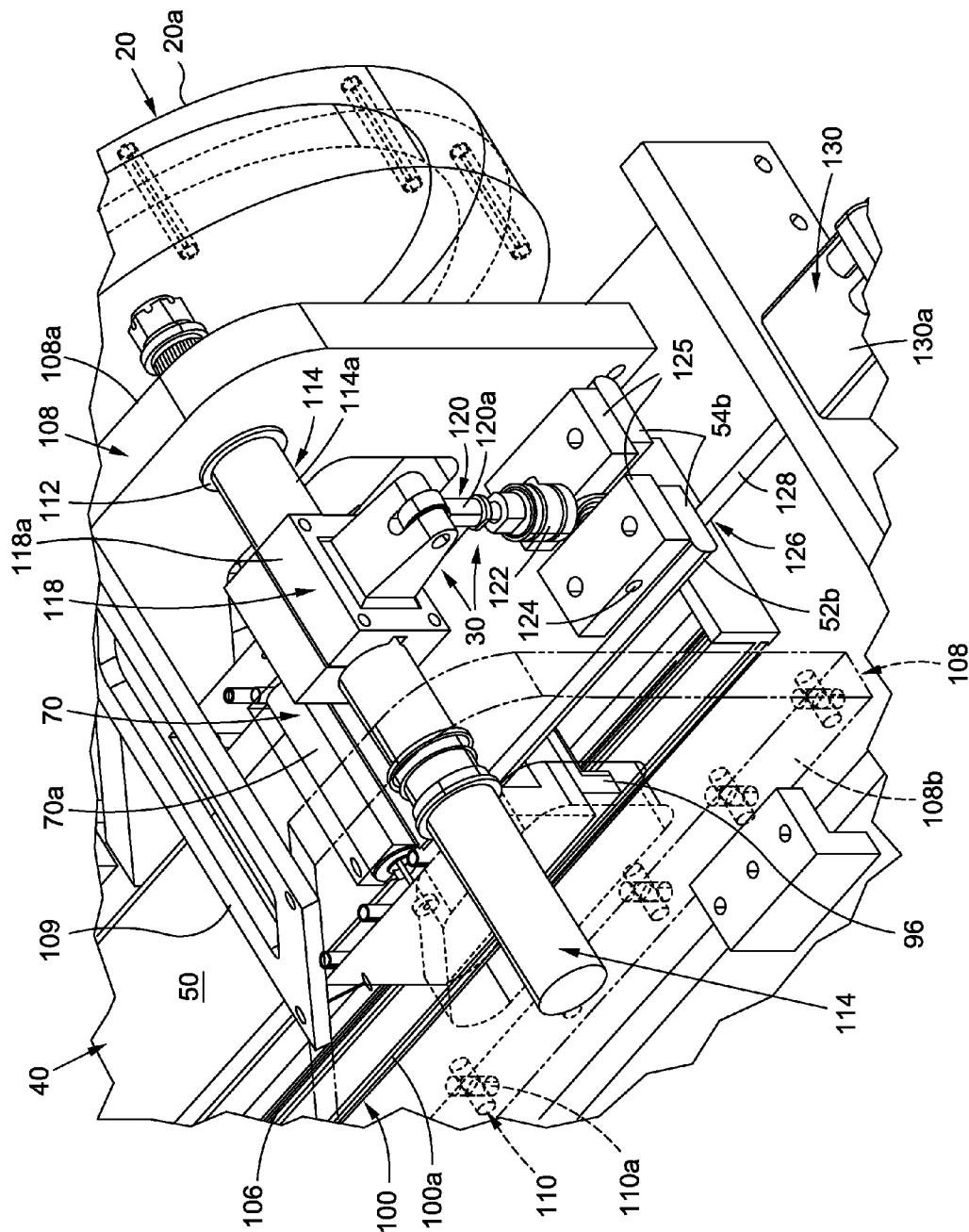
FIG. 1D is an illustration of a close-up back perspective view of the aerodynamic load simulator of FIG. 1C.
Figure 1E:
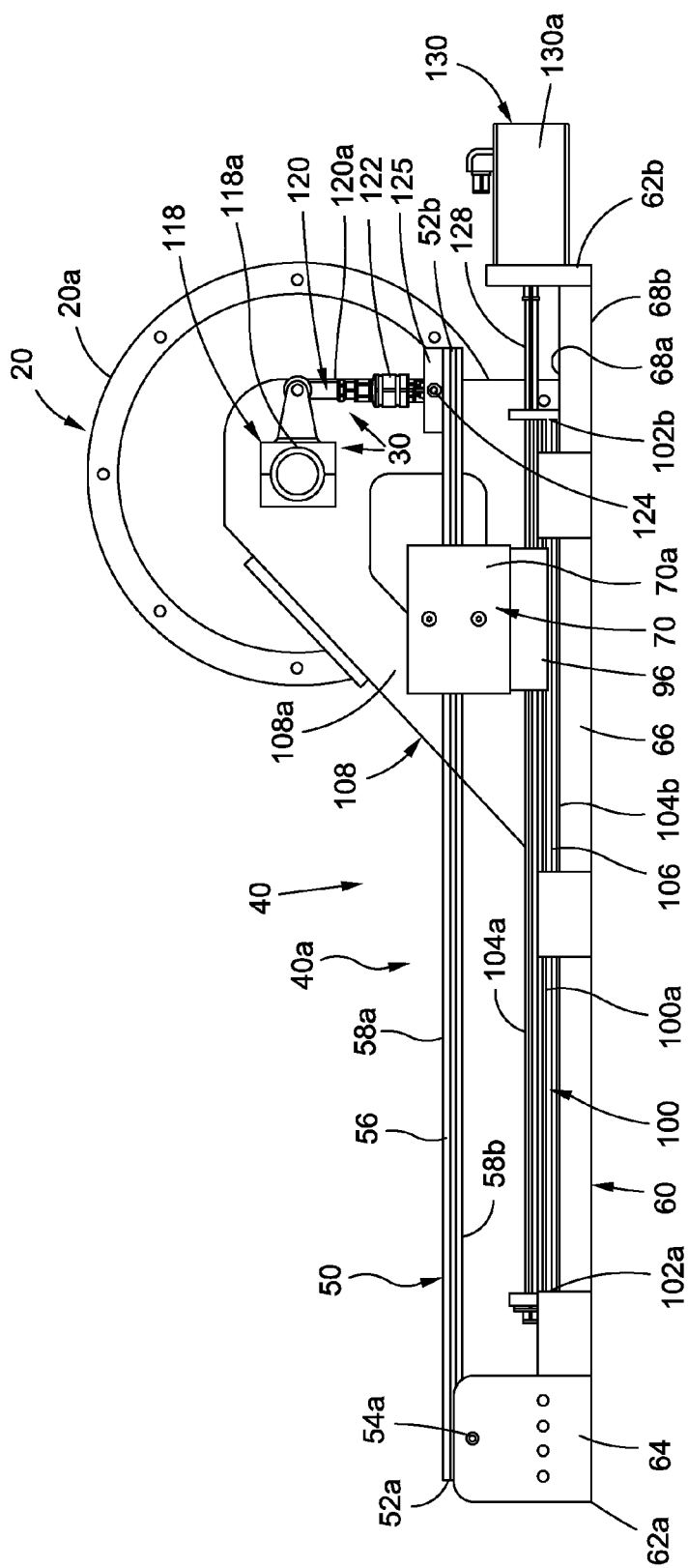
FIG. 1E is an illustration of a cross-sectional view taken along lines 1E-1E of FIG. 1B.

FIG. 1B is an illustration of a close-up front perspective view of an embodiment of the aerodynamic load simulator 30 with the continuously adjustable spring rate constant assembly 40 of the flight control test simulator system 10 of FIG. 1A. FIG. 1C is an illustration of a close-up side perspective view of the aerodynamic load simulator 30 of FIG. 1B. FIG. 1D is an illustration of a close-up back perspective view of the aerodynamic load simulator 30 of FIG. 1C. FIG. 1E is an illustration of a cross-sectional view taken along lines 1E-1E of FIG. 1B of the flight control test simulator system 10 of FIG. 1B.

As shown in FIGS. 1A-1E, the flight control assembly 12 further comprises a simulated surface 20. The simulated surface 20 (see FIGS. 1A-1E, 5) may comprise a rotating flywheel 20a (see FIGS. 1A-1E, 5) or a flight control inertia mass simulator 20b (see FIG. 5), or another suitable simulated surface. The simulated surface 20 may be of any suitable shape and size sufficient to simulate an aerodynamic surface of an aircraft component.

Alternatively, the flight control assembly 12 (see FIGS. 1A-1E, 5) may comprise at least one flight control surface 22 (see FIG. 5). The flight control surface 22 (see FIG. 5) may comprise, for example, an aircraft component 22a, such as an aircraft rudder, an aircraft elevator, or another suitable aircraft component.

As shown in FIGS. 1A and FIG. 5, the flight control test simulator system 10, such as in the form of aircraft flight control test simulator system 10a, may further comprise a test piece 24, such as in the form of an aircraft test piece 24a. The aircraft test piece 24a may comprise, for example, a wing spar, or another suitable aircraft test piece. A flight control test 25 (see FIG. 5) is preferably conducted on the test piece 24 (see FIG. 5) using the flight control assembly 12 (see FIG. 5) and the aerodynamic load simulator 30 (see FIG. 5) of the flight control test simulator system 10 (see FIG. 5).

As shown in FIG. 1A, the flight control test simulator system 10, such as in the form of aircraft flight control test simulator system 10a, may further comprise mounting structures 26, such as, for example, metal strongback beams or girders, or other support structures that are sufficiently strong and sturdy for mounting the aerodynamic load simulator 30 with the continuously adjustable spring rate constant assembly 40. As shown in FIG. 1A, the aerodynamic load simulator 30 with the continuously adjustable spring rate constant assembly 40 may be mounted or attached to the exterior of each mounting structure 26 with one or more mounting elements 28. The one or more mounting elements 28 may comprise, for example, brackets or clamps with attachment elements such as screws or bolts, or other suitable mounting elements or devices. The aerodynamic load simulator 30 with the continuously adjustable spring rate constant assembly 40 may be mounted or attached at various locations on the mounting structure 26 in order to simulate movement of aerodynamic surfaces of aircraft components, such as for example, aircraft elevator trim, aircraft stabilizer trim, or other moveable aerodynamic surfaces of aircraft components. The continuously adjustable spring rate constant assembly 40 may preferably be detachable from the simulated surface 20 (see FIGS. 1A-1E, 5) or the at least one flight control surface 22 (see FIG. 5) to allow for unobstructed surface travel.

Figure 2A:
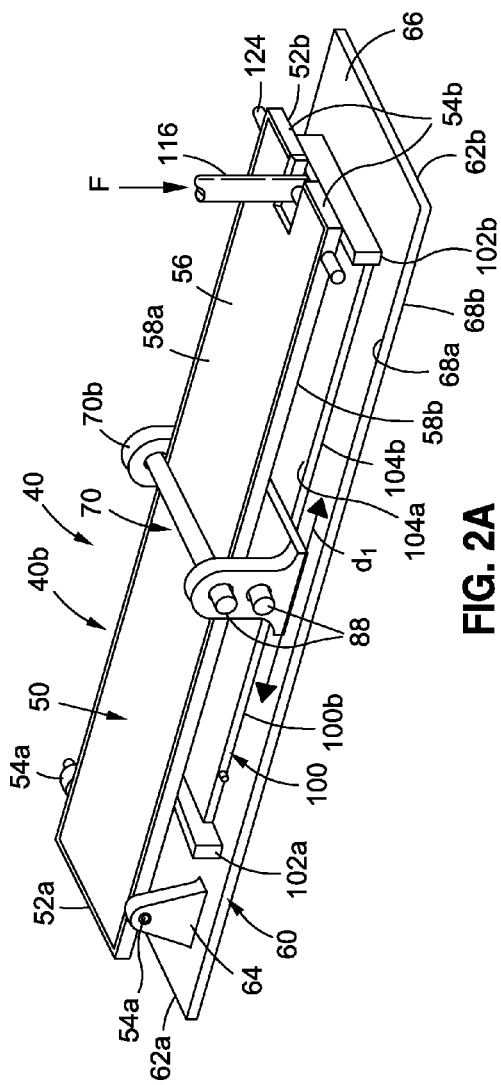
FIG. 2A is an illustration of a side perspective view of another embodiment of a continuously adjustable spring rate constant assembly that may be used in the flight control test simulator system of the disclosure.
Figure 2B:
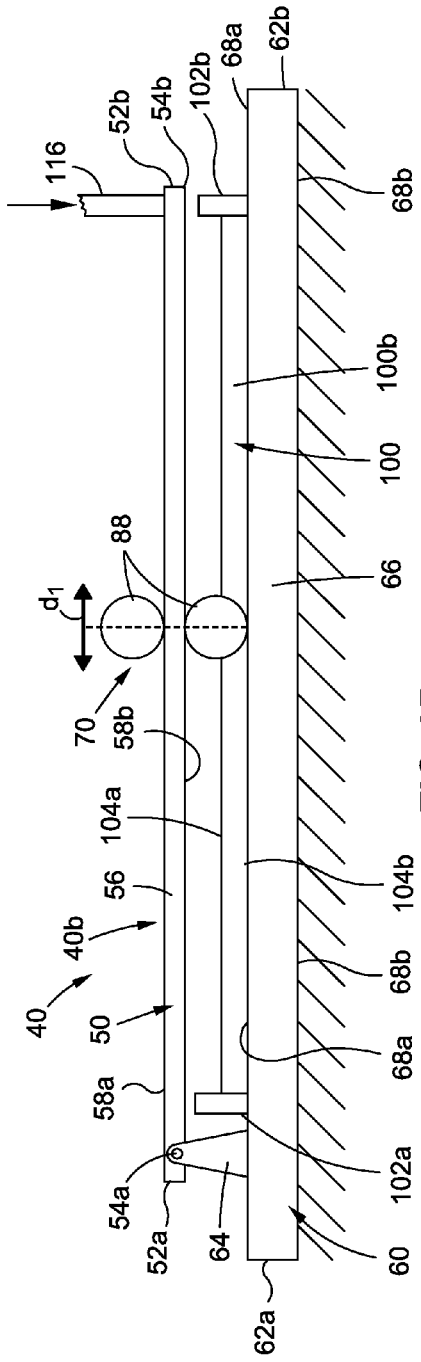
FIG. 2B is an illustration of a schematic side view of the continuously adjustable spring rate constant assembly of FIG. 2A.

In one embodiment, the continuously adjustable spring rate constant assembly 40 (see FIGS. 1A, 1E) may be in the form of continuously adjustable spring rate constant assembly 40a (see FIGS. 1A, 1E). In another embodiment, the continuously adjustable spring rate constant assembly 40 (see FIGS. 2A, 5) may be in the form of continuously adjustable spring rate constant assembly 40b (see FIG. 2A). FIG. 2A is an illustration of a side perspective view of the continuously adjustable spring rate constant assembly 40, such as in the form of continuously adjustable spring rate constant assembly 40b, that may be used in the flight control test simulator system 10 (see FIG. 5) of the disclosure. FIG. 2B is an illustration of a schematic side view of the continuously adjustable spring rate constant assembly 40, such as in the form of continuously adjustable spring rate constant assembly 40b, of FIG. 2A.

The continuously adjustable spring rate constant assembly 40 (see FIGS. 1A, 1E, 2A), such as in the form of continuously adjustable spring rate constant assembly 40a (see FIGS. 1A, 1E), or in the form of continuously adjustable spring rate constant assembly 40b (see FIG. 2A), comprises a beam spring 50 (see FIGS. 1A, 1E, 2A). As shown in FIGS. 1A, 1E, 2A, the beam spring 50 comprises a first fixed end 52a and a second non-fixed end 52b. Fixed points 54a (see FIGS. 1B, 2A) at the first fixed end 52a (see FIGS. 1B, 2A) fix the beam spring 50 (see FIGS. 1B, 2A) to a base member 60 (see FIGS. 1B, 2A) via anchor members 64 (see FIGS. 1B, 2A). Free points 54b (see FIGS. 1B, 2A) at the second non-fixed end 52b (see FIGS. 1B, 2A) allow the second non-fixed end 52b (see FIGS. 1B, 2A) of the beam spring 50 (see FIGS. 1B, 2A) to move freely up and down. Thus, the beam spring 50 (see FIGS. 1E, 2A) preferably has a pinned and simply supported design in which the beam spring 50 (see FIGS. 1E, 2A) is pinned at only the first fixed end 52a (see FIGS. 1E, 2A) and simply supported at only the adjustable fulcrum assembly 70 (see FIGS. 1E, 2A).

The beam spring 50 (see FIGS. 1E, 2A) further comprises a body 56 (see FIGS. 1E, 2A), a first top side 58a (see FIGS. 1E, 2A), and a second bottom side 58b (see FIGS. 1E, 2A). The body 56 (see FIGS. 1E, 2A) of the beam spring 50 (see FIGS. 1E, 2A) preferably has an elongated, substantially flat, rectangular shape. However, the body 56 (see FIGS. 1E, 2A) of the beam spring 50 (see FIGS. 1E, 2A) may also be of other suitable shapes.

The beam spring 50 (see FIGS. 1E, 2A) may be of any desired size or may be sized according to the size of the simulated surface 20 (see FIGS. 1A, 1E) or the flight control surface 22 (see FIG. 5) used in the flight control test simulator system 10. Preferably, the beam spring 50 (see FIGS. 1E, 2A) is made of a metal material, such as spring steel, titanium or another suitable metal material, a composite material, or another suitable material.

The beam spring 50 (see FIGS. 1A-1E, 2A-2B, 5) has a spring rate 44 (see FIG. 5). As used herein, the term "spring rate" means the amount of force required to compress a spring, such as herein the beam spring 50 (see FIGS. 1A-1E, 2A-2B, 5), a certain distance, for example, compressing a spring one inch. In general, the lower the spring rate, the softer the spring, and the higher the spring rate, the stiffer the spring.

The beam spring 50 (see FIGS. 1A-1E, 2A-2B, 5) preferably has an adjustable spring rate 44a (see FIG. 5), and more preferably has an automated adjustable spring rate 44b (see FIG. 5). The adjustable spring rate 44a (see FIG. 5), and more preferably, the automated adjustable spring rate 44b (see FIG. 5), are adjustable in real time and under aerodynamic load 32 (see FIG. 5) via an analog input/command signal 48 (see FIG. 5). The analog input/command signal 48 (see FIG. 5) may comprise a computer input 48a (see FIG. 5), a manual input 48b (see FIG. 5), or another suitable analog input/command signal. The aerodynamic load 32 (see FIG. 5) may be simulated by the aerodynamic load simulator 30 (see FIGS. 1A, 5) to obtain a simulated continuous aerodynamic load 32a (see FIG. 5).

The beam spring 50 (see FIGS. 1A-1E, 2A-2B, 5) further has a spring rate constant 42 (see FIG. 5). As used herein, the term "spring rate constant" means the change in the force a spring, such as herein the beam spring 50 (see FIGS. 1A-1E, 2A-2B), exerts, divided by the change in deflection of the spring, such as herein the beam spring 50 (see FIGS. 1A-1E, 2A-2B). The spring rate constant is the gradient of a force versus deflection curve.

The continuously adjustable spring rate constant assembly 40 (see FIGS. 1A, 5) of the aerodynamic load simulator 30 (see FIGS. 1A, 5) is preferably configured to adjust, over a range of predetermined flight profiles 46a (see FIG. 5), the spring rate constant 42 (see FIG. 5) of the simulated continuous aerodynamic load 32a (see FIG. 5) adjustably induced on the flight control assembly 12 (see FIGS. 1A, 5). As used herein, "simulated continuous aerodynamic load" means a load applied in a continuous manner and simulating that of an aerodynamic load, for example, aerodynamic load 32 (see FIG. 5). The flight control test simulator system 10 (see FIGS. 1A, 5) with the continuously adjustable spring rate constant assembly 40 (see FIGS. 1A, 2A, 5) provides an automated system for modifying the aerodynamic load 32 (see FIG. 5) during testing, for adjusting an aerodynamic load condition 34 (see FIG. 5) during testing, and for adjusting the spring rate 44 (see FIG. 5) during testing.

The continuously adjustable spring rate constant assembly 40 (see FIGS. 1A, 1E, 2A), such as in the form of continuously adjustable spring rate constant assembly 40a (see FIGS. 1A, 1E), or in the form of continuously adjustable spring rate constant assembly 40b (see FIG. 2A), further comprises a base member 60, such as a frame or plate, for supporting the beam spring 50 (see FIGS. 1A-1B, 1E, 2A-2B) of the continuously adjustable spring rate constant assembly 40 (see FIGS. 1A, 1E, 2A). As shown in FIG. 1A, the base member 60 may be attached to the mounting structure 26 with mounting elements 28, as discussed in more detail above.

As shown in FIGS. 1A-1B, 1E, 2A-2B, the base member 60 comprises a first end 62a and a second end 62b. As further shown in FIGS. 1A-1B, 1E, 2A-2B, anchor members 64 positioned at the first end 62a of the base member 60 are preferably used to connect or fix the first fixed end 52a of the beam spring 50 to the first end 62a of the base member 60.

When the continuously adjustable spring rate constant assembly 40 (see FIGS. 1A, 1E, 2A) is assembled, the beam spring 50 (see FIGS. 1A-1B, 1E, 2A-2B) is preferably aligned longitudinally with and positioned in a spaced relationship over the base member 60 (see FIGS. 1E, 2A-2B).

As shown in FIGS. 1E and 2A-2B, the base member 60 comprises a body 66, a first top side 68a, and a second bottom side 68b. The body 66 (see FIGS. 1E, 2A-2B) of the base member 60 (see FIGS. 1E, 2A-2B) preferably has an elongated, substantially flat, rectangular shape. However, the body 66 (see FIGS. 1E, 2A-2B) of the base member 60 (see FIGS. 1E, 2A-2B) may also be of other suitable shapes.

The base member 60 (see FIGS. 1E, 2A-2B) may be of any desired size or may be sized according to the size of the beam spring 50 (see FIGS. 1A-1B, 1E, 2A-2B) or the continuously adjustable spring rate constant assembly 40 (see FIGS. 1A, 1E, 2A) used in the flight control test simulator system 10. Preferably, the base member 60 (see FIGS. 1E, 2A-2B) is made of a metal material, such as steel or another suitable metal material, a composite material, or another suitable material.

The continuously adjustable spring rate constant assembly 40 (see FIGS. 1A, 1E, 2A), such as in the form of continuously adjustable spring rate constant assembly 40a (see FIGS. 1A, 1E), or in the form of continuously adjustable spring rate constant assembly 40b (see FIG. 2A), further comprises an adjustable fulcrum assembly 70 (see FIGS. 1B, 1D, 1E, 2A-2B) coupled to the beam spring 50 (see FIGS. 1B, 1D, 1E, 2A-2B). The adjustable fulcrum assembly 70 (see FIGS. 1B, 1D, 1E, 2A-2B) is configured to move lengthwise along the beam spring 50 (see FIGS. 1B, 1D, 1E, 2A-2B) between the first fixed end 52a (see FIGS. 1B, 1E, 2A-2B) and the second non-fixed end 52b (see FIGS. 1B, 1E, 2A-2B) of the beam spring 50 (see FIGS. 1B, 1E, 2A-2B) to create contact between the beam spring 50 (see FIGS. 1B, 1E, 2A-2B) and the base member 60 (see FIGS. 1B, 1E, 2A-2B).

Figure 3A:
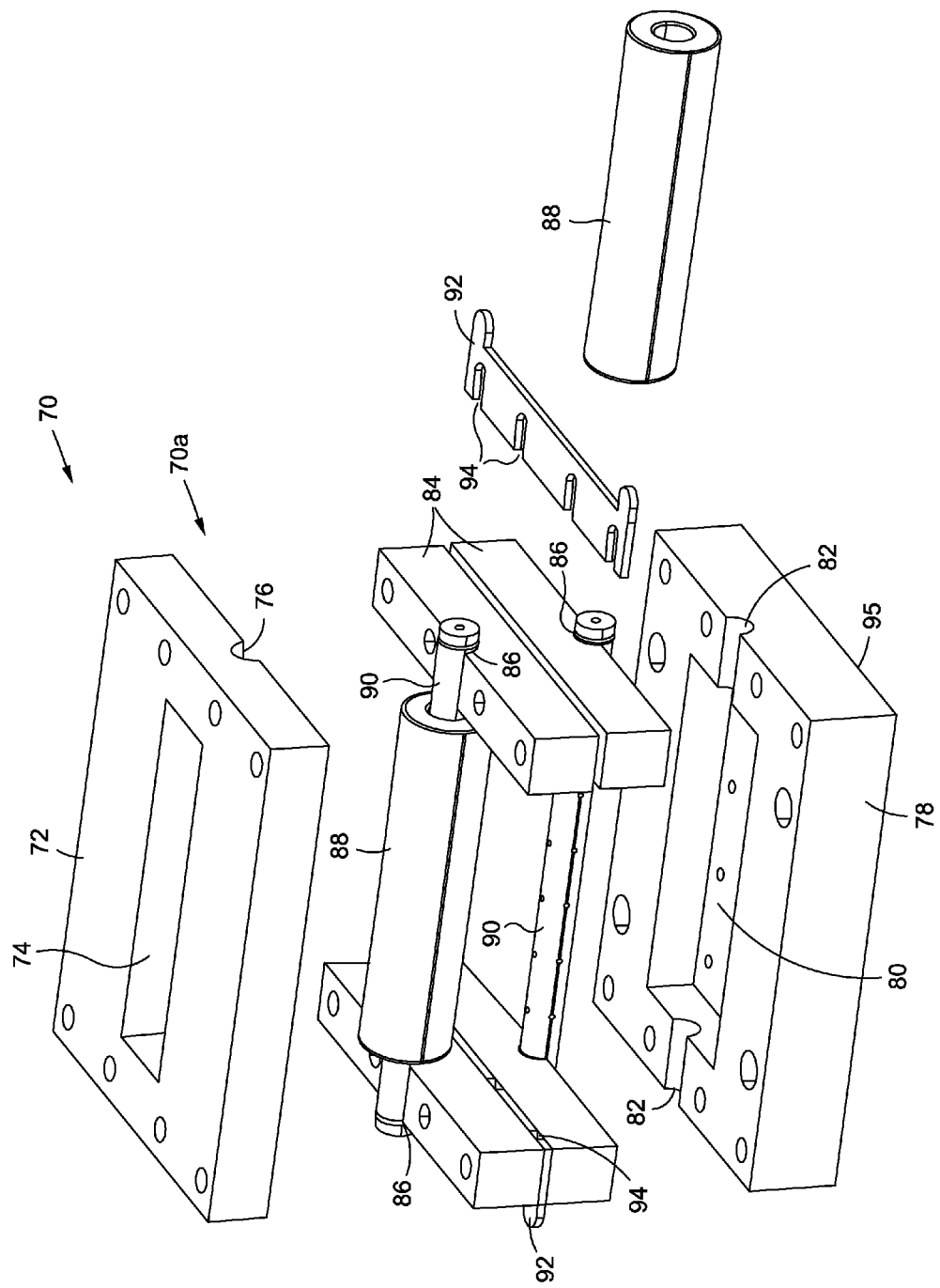
FIG. 3A is an illustration of an exploded front perspective view of an adjustable fulcrum assembly that may be used in the flight control test simulator system and method of the disclosure.

In one embodiment, the adjustable fulcrum assembly 70 (see FIGS. 1B, 1D, 1E) may be in the form of adjustable fulcrum assembly 70a (see FIGS. 1B, 1D, 1E). FIG. 3A is an illustration of an exploded front perspective view of the adjustable fulcrum assembly 70, such as in the form of adjustable fulcrum assembly 70a, that may be used in the flight control test simulator system 10 of the disclosure. FIG. 3B is an illustration of an assembled front perspective view of the adjustable fulcrum assembly 70, such as in the form of adjustable fulcrum assembly 70a, of FIG. 3A. FIG. 3C is an illustration of an assembled front view of the adjustable fulcrum assembly 70, such as in the form of adjustable fulcrum assembly 70a, of FIG. 3B.

As shown in FIGS. 3A-3C, the adjustable fulcrum assembly 70, such as in the form of adjustable fulcrum assembly 70a, comprises an upper plate 72. The upper plate 72 (see FIGS. 3A-3C) preferably has an elongated opening 74 (see FIGS. 3A-3B) and one or more upper plate notches 76 (see FIG. 3A).

As shown in FIGS. 3A-3C, the adjustable fulcrum assembly 70, such as in the form of adjustable fulcrum assembly 70a, further comprises a lower plate 78. The lower plate 78 (see FIGS. 3A-3C) preferably has a recessed portion 80 (see FIGS. 3A-3B) and one or more lower plate notches 82 (see FIG. 3A).

As shown in FIGS. 3A-3C, the adjustable fulcrum assembly 70, such as in the form of adjustable fulcrum assembly 70a, further comprises one or more spacer plates 84. Each spacer plate 84 (see FIGS. 3A-3C) preferably has one or more spacer plate notches 86 (see FIG. 3A).

As shown in FIGS. 3A-3C, the adjustable fulcrum assembly 70, such as in the form of adjustable fulcrum assembly 70a, further comprises one or more roller members 88. Each roller member 88 (see FIGS. 3A-3C) may have an elongated axle 90 (see FIGS. 3A-3C) inserted through the roller member 88. The ends of the elongated axle 90 (see FIG. 3A) are preferably configured to be cradled within the spacer plate notches 86 (see FIG. 3A) formed in the spacer plates 84 (see FIG. 3A).

As shown in FIGS. 1D, 1E, when the continuously adjustable spring rate constant assembly 40 is assembled, the beam spring 50 is inserted through the adjustable fulcrum assembly 70, and the adjustable fulcrum assembly 70 is positioned between the first top side 58a and the second bottom side 58b of the beam spring 50, and the first top side 68a of the base member 60. Preferably, the beam spring 50 (see FIG. 1E) is inserted between roller members 88 (see FIG. 3C) of the adjustable fulcrum assembly 70 (see FIG. 3C).

As shown in FIGS. 3A-3C, the adjustable fulcrum assembly 70, such as in the form of adjustable fulcrum assembly 70a, further comprises one or more shim members 92. Each shim member 92 (see FIGS. 3A-3C) preferably has one or more shim notches 94 (see FIG. 3A). Each shim member 92 (see FIGS. 3A-3C) is preferably positioned between the spacer plates 84 (see FIGS. 3A-3C).

In another embodiment, the adjustable fulcrum assembly 70 (FIGS. 1B, 1D, 1E) may be in the form of adjustable fulcrum assembly 70b (FIG. 2A). As shown in FIGS. 2A-2B, when the continuously adjustable spring rate constant assembly 40, such as in the form of continuously adjustable spring rate constant assembly 40b, is assembled, the beam spring 50 is inserted through the adjustable fulcrum assembly 70b, and the adjustable fulcrum assembly 70b is positioned between the first top side 58a and the second bottom side 58b of the beam spring 50, and the first top side 68a of the base member 60. Preferably, the beam spring 50 (see FIGS. 2A-2B) is inserted between roller members 88 (see FIGS. 2A-2B) of the adjustable fulcrum assembly 70b (see FIGS. 2A-2B).

The continuously adjustable spring rate constant assembly 40 (see FIGS. 1B, 1D, 1E, 2A-2B), such as in the form of continuously adjustable spring rate constant assembly 40a (see FIGS. 1B, 1D, 1E), or in the form of continuously adjustable spring rate constant assembly 40b (see FIGS. 2A-2B), further comprises a positioning device 100 (see FIGS. 1B, 1D, 1E, 2A-2B) attached to the base member 60 (see FIGS. 1B, 1E, 2A-2B). The positioning device 100 (see FIGS. 1B, 1D, 1E, 2A-2B) is preferably positioned between the base member 60 (see FIGS. 1B, 1E, 2A-2B) and the beam spring 50 (see FIGS. 1B, 1E, 2A-2B). The beam spring 50 (see FIGS. 1A-1B, 1E, 2A-2B) is preferably aligned longitudinally with and positioned in a spaced relationship over the positioning device 100 (see FIGS. 1B, 1D, 1E, 2A-2B).

Figure 4:
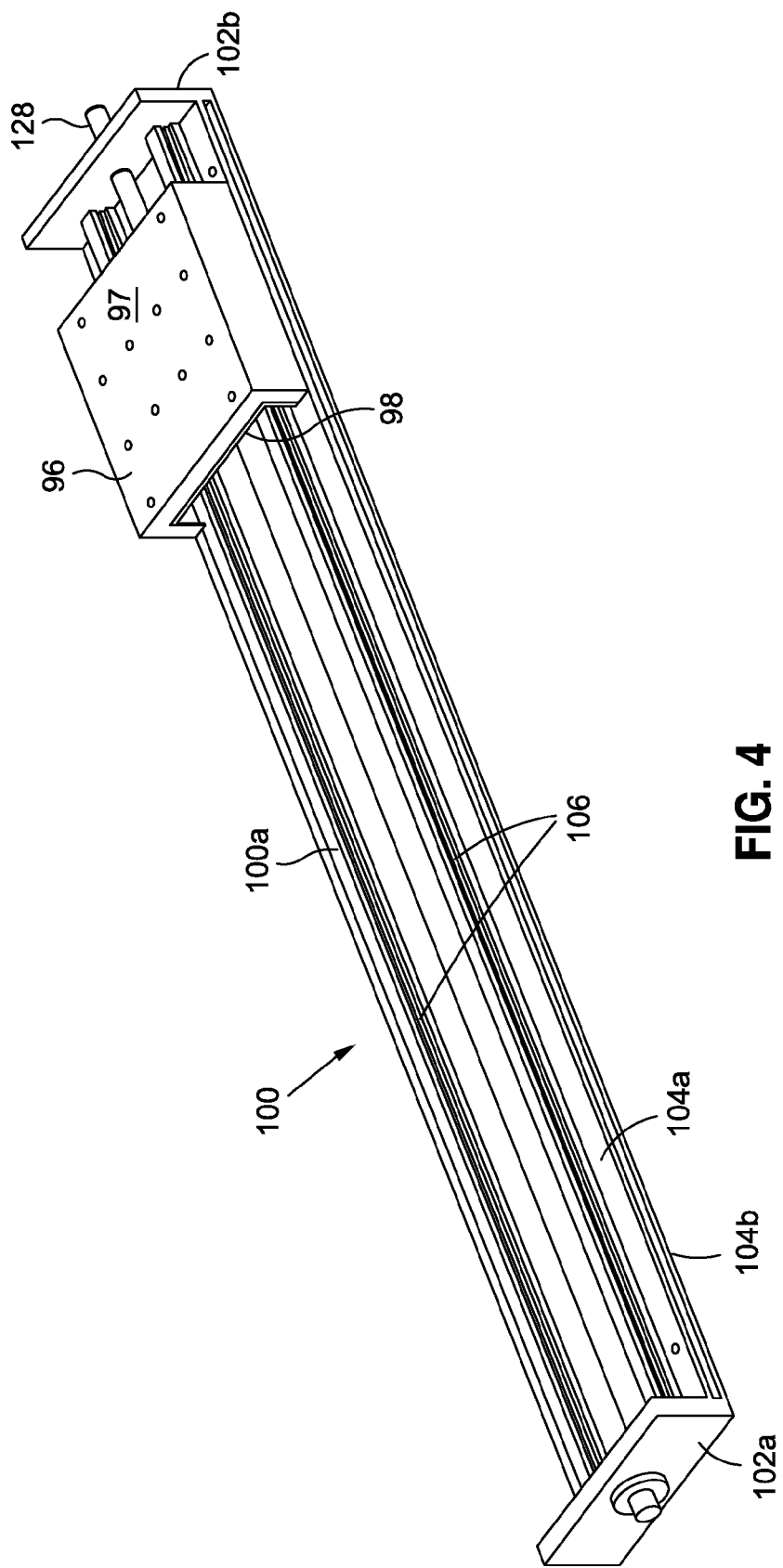
FIG. 4 is an illustration of a side perspective view of a positioning device that may be used in the flight control test simulator system and method of the disclosure.

In one embodiment, the positioning device 100 (FIGS. 1B, 1D, 1E) may be in the form of a sliding device 100a (FIGS. 1B, 1D, 1E) that is automated. FIG. 4 is an illustration of a side perspective view of the positioning device 100, such as in the form of sliding device 100a, that may be used in the flight control test simulator system 10 of the disclosure.

As shown in FIG. 4, the positioning device 100, such as in the form of a sliding device 100a, has a sliding portion 96. The sliding portion 96 preferably has an inverted U-shaped configuration. However, the sliding portion 96 may also be of another suitable shape. The sliding portion 96 (see FIG. 4) has an opening 98 (see FIG. 4) preferably also having an inverted U-shaped configuration. However, the opening 98 (see FIG. 4) may also be of another suitable shape. A bottom surface 95 (see FIGS. 3A-3C) of the adjustable fulcrum assembly 70 (see FIGS. 3A-3C) is preferably stacked over and attached to a top surface 97 (see FIG. 4) of the sliding portion 96, when the continuously adjustable spring rate constant assembly 40 is assembled.

As further shown in FIG. 1E and FIG. 4, the positioning device 100, such as in the form of sliding device 100a, has a first end 102a, a second end 102b, a first top side 104a, a second bottom side 104b, and a pair of tracks 106. The opening 98 (see FIG. 4) of the sliding portion 96 (see FIG. 4) is preferably configured to slide along the exterior of the pair of tracks 106 (see FIG. 4), when the continuously adjustable spring rate constant assembly 40 is assembled.

As shown in FIG. 1E, when the continuously adjustable spring rate constant assembly 40, such as in the form of continuously adjustable spring rate constant assembly 40b, is assembled, the positioning device 100, such as in the form of sliding device 100a, is attached to and positioned between the first top side 68a of the base member 60 and the adjustable fulcrum assembly 70, such as in the form of adjustable fulcrum assembly 70a. As further shown in FIG. 1E, the beam spring 50 is preferably aligned with and positioned over the positioning device 100, such as in the form of sliding device 100a.

In another embodiment, the positioning device 100 (FIGS. 2A-2B) may be in the form of a sliding device 100b (FIGS. 2A-2B). As shown in FIGS. 2A-2B, when the continuously adjustable spring rate constant assembly 40, such as in the form of continuously adjustable spring rate constant assembly 40b, is assembled, the positioning device 100, such as in the form of sliding device 100b, is attached to and positioned between the first top side 68a of the base member 60 and the adjustable fulcrum assembly 70, such as in the form of adjustable fulcrum assembly 70b. As further shown in FIGS. 2A-2B, the beam spring 50 is preferably aligned with and positioned over the positioning device 100, such as in the form of sliding device 100b.

The positioning device 100 (see FIGS. 1E, 2A) creates contact between portions of the beam spring 50 (see FIGS. 1E, 2A) and the base member 60 (see FIGS. 1E, 2A) in order to determine the variable stiffness of the beam spring 50 (see FIGS. 1E, 2A) with continuity. The adjustable fulcrum assembly 70 (see FIGS. 1E, 2A) slides lengthwise along the positioning device 100 (see FIGS. 1E, 2A) between the first end 102a (see FIGS. 1E, 2A) and the second end 102b (see FIGS. 1E, 2A) of the positioning device 100 (see FIGS. 1E, 2A), and between the fixed points 54a (see FIGS. 1B, 2A) and the free points 54b (see FIGS. 1B, 2A) of the beam spring 50 (see FIGS. 1B, 2A). As shown in FIGS. 2A-2B, the adjustable fulcrum assembly 70 (see FIGS. 1E, 2A) slides lengthwise along the positioning device 100 (see FIGS. 1E, 2A) and along the beam spring 50 in a lengthwise direction $d_1$.

The continuously adjustable spring rate constant assembly 40 (see FIGS. 1A-1E, 5) further comprises support elements 108 (see FIGS. 1A-1E, 5), such as in the form of hinge line trunnion elements 108a, 108b (see FIGS. 1A-1E, 5). The support elements 108 (see FIGS. 1A-1E, 5), such as in the form of hinge line trunnion element 108a, 108b (see FIGS. 1A-1E, 5), are preferably coupled to the base member 60 (see FIGS. 1A, 1B, 1E, 5), and are preferably positioned on each side of the beam spring 50 (see FIGS. 1A, 1B, 5).

A connector element 109 (see FIGS. 1A-1C) connects together the support elements 108 (see FIGS. 1A-1E, 5), such as in the form of hinge line trunnion elements 108a, 108b (see FIGS. 1A-1E, 5), and forms a bridge between the support elements 108 (see FIGS. 1A-1E, 5), such as in the form of hinge line trunnion elements 108a, 108b (see FIGS. 1A-1E, 5).

The support elements 108 (see FIGS. 1A, 1D), such as in the form of hinge line trunnion element 108a, 108b (see FIGS. 1A, 1D), are preferably attached to the base member 60 (see FIG. 1A) via attachment elements 110 (see FIG. 1D). The attachment elements 110 (see FIG. 1D) may comprise bolts 110a (see FIG. 1D), screws (not shown), or another suitable attachment element.

The support elements 108 (see FIGS. 1A-1D), such as in the form of hinge line trunnion element 108a, 108b (see FIGS. 1A-1D), preferably each have a through opening 112 (see FIGS. 1A-1D) configured for insertion of the shaft 114 (see FIGS. 1A-1D). The shaft 114 (see FIGS. 1A-1D) preferably comprises a crank shaft 114a (see FIGS. 1B-1D). The shaft 114 (see FIGS. 1A-1D) connects the simulated surface 20 (see FIGS. 1A-1D) of the flight control assembly 12 (see FIGS. 1A-1D) to the aerodynamic load simulator 30 (see FIGS. 1A-1B, 1D-1E) and to the test piece 24 (see FIG. 1A).

As shown in FIGS. 1A-1C, FIGS. 2A-2B, and FIG. 5, the flight control test simulator system 10, and in particular, the aerodynamic load simulator 30 of the flight control test simulator system 10, further comprises an input assembly 116. The input assembly 116 (see FIGS. 1A-1C, 2A-2B, 5) is preferably configured to input a tensile load 36 (see FIG. 5) and a compressive load 38 (see FIG. 5) from the simulated surface 20 (see FIGS. 1A-1C, 5) to the continuously adjustable spring rate constant assembly 40 (see FIGS. 1A, 5), and in particular, to the beam spring 50 (see FIGS. 1A-1E, 2A-2B, 5). Thus, the simulated surface 20 (see FIGS. 1A, 5) acts as a force system capable of inputting a force or load, such as a tensile load 36 (see FIG. 5) and/or a compressive load 38 (see FIG. 5), via the input assembly 116 (see FIGS. 2A-2B) to the beam spring 50 (see FIGS. 2A-2B).

As used herein, the term "tensile load" means a force that attempts to pull apart or stretch a material or structure, such as herein the beam spring 50 (see FIGS. 1A-1E, 2A-2B). The beam spring 50 (see FIGS. 1A-1E, 2A-2B) is designed to support tensile loads.

As used herein, the term "compressive load" means a force or pressure that attempts to flatten or squeeze a material or structure, such as herein, the beam spring 50 (see FIGS. 1A-1E, 2A-2B). The beam spring 50 (see FIGS. 1A-1E, 2A-2B) is designed to support compressive loads.

The input assembly 116 (see FIGS. 1A-1C, 5) of the aerodynamic load simulator 30 preferably comprises a crank element 118 (see FIGS. 1A-1E, 5), such as in the form of a first crank element 118a (see FIGS. 1A-1E, 5). The first crank element 118a (see FIGS. 1A-1E, 5) is preferably connected to a tie rod element 120 (see FIGS. 1B-1E, 5), such as in the form of a first tie rod 120a (see FIGS. 1B-1E, 5). The tie rod element 120 (see FIGS. 1B-1E, 5), such as in the form of first tie rod 120a (see FIGS. 1B-1E, 5), is preferably connected to a load cell 122 (see FIGS. 1B-1E, 5). As further shown in FIGS. 1B-1D, the first crank element 118a, the first tie rod 120a, and the load cell 122 preferably connect the simulated surface 20 via shaft 114 to the beam spring 50.

The input assembly 116 (see FIGS. 1A-1C, 5) of the aerodynamic load simulator 30 may further comprise a crank element 118 (see FIGS. 1A-1E, 5), such as in the form of a second crank element 118b (see FIGS. 1A-1E, 5). The second crank element 118b (see FIGS. 1A-1E, 5) is preferably connected to a tie rod element 120 (see FIGS. 1B-1E, 5), such as in the form of a second tie rod 120b (see FIGS. 1B-1E, 5). As further shown in FIGS. 1A-1C, the second crank element 118b and the second tie rod 120b connect the simulated surface 20 via shaft 114 to the test piece 24.

As shown in FIGS. 1C-1D, the load cell 122 is preferably coupled to the beam spring 50 via a connector shaft 124 and anchor elements 125. The connector shaft 124 (see FIGS. 1C-1D) is preferably inserted through the anchor elements 125 (see FIGS. 1C-1D).

The continuously adjustable spring rate constant assembly 40 (see FIGS. 1B, 1D, 5) further comprises a drive mechanism 126 (see FIGS. 1B, 1D, 5) configured to move the adjustable fulcrum assembly 70 (see FIGS. 1B, 1D, 5) lengthwise along the positioning device 100 (see FIGS. 1B, 1D, 5). The drive mechanism 126 (see FIGS. 1B, 1D, 5) preferably comprises a screw element 128 (see FIGS. 1B, 1D, 5) attached to the adjustable fulcrum assembly 70 (see FIGS. 1B, 1D, 5). The screw element 128 (see FIGS. 1B, 1D, 5) is preferably driven by a power supply 130 (see FIGS. 1A-B, 1D-1E, 5). The power supply 130 (see FIGS. 1A-B, 1D-1E, 5) preferably comprises an electric motor 130a (see FIGS. 1A-B, 1D-1E, 5). However, the power supply 130 (see FIGS. 1A-B, 1D-1E, 5) may comprise a pneumatic power supply, a hydraulic power supply, or another suitable power supply for supplying power to the drive mechanism 126 (see FIGS. 1B, 1D, 5).

As shown in FIGS. 2A-2B, the input assembly 116 is coupled at one end to the second non-fixed end 52b of the beam spring 50 via the connector shaft 124. The input assembly 116 (see FIGS. 2A-2B) is preferably coupled at the other end to the simulated surface (not shown), such as the simulated surface 20 (see FIGS. 1A, 5). The simulated surface 20 (see FIGS. 1A, 5) acts as a force system capable of inputting a force F↓ (see FIGS. 2A-2B) via the input assembly 116 (see FIGS. 2A-2B), such as a tensile load 36 (see FIG. 5) and/or a compressive load 38 (see FIG. 5), to the beam spring 50 (see FIGS. 2A-2B).

In another embodiment of the disclosure there is provided an aircraft flight control test simulator system 10a for testing a simulated surface 20 or a flight control surface 22. FIG. 5 is an illustration of a block diagram of an exemplary embodiment of a flight control test simulator system 10, such as in the form of an aircraft flight control test simulator system 10a, of the disclosure. As shown in FIG. 5, and as discussed in detail above, the flight control test simulator system 10, such as in the form of an aircraft flight control test simulator system 10a, comprises a mounting structure 26 with mounting elements 28.

The aircraft flight control test simulator system 10a (see FIG. 5) is preferably automated and comprises a flight control assembly 12 (see FIG. 5) having at least one actuator 14 (see FIG. 5), having a flight controller 16 (see FIG. 5) configured to actuate the at least one actuator 14 (see FIG. 5). As shown in FIG. 5, the aircraft flight control test simulator system 10a further comprises a processing device 18, such as in the form of a computer 18a, or another suitable processing device.

In one embodiment as shown in FIG. 5, the aircraft flight control test simulator system 10a may comprise the simulated surface 20 comprising, for example, a rotating flywheel 20a, or a flight control inertia mass simulator 20b. In another embodiment as shown in FIG. 5, the aircraft flight control test simulator system 10a may comprise the flight control surface 22 comprising, for example, an aircraft component 22a.

As shown in FIG. 5, the flight control assembly 12 further comprises a test piece 24 (see also FIG. 1A) comprising, for example, an aircraft test piece 24a (see also FIG. 1A). The flight control assembly 12 (see FIG. 5) is preferably used for a flight control test 25 (see FIG. 5). One or more flight profiles 46 (see FIG. 5) may be determined for the flight control test 25 (see FIG. 5). The flight control test 25 (see FIG. 5) is preferably performed to simulate a portion of a flight of an aircraft 200a (see FIG. 7).

As shown in FIG. 5, the aircraft flight control test simulator system 10a further comprises an aerodynamic load simulator 30 coupled to the flight control assembly 12 and configured to adjustably induce a simulated continuous aerodynamic load 32a on the flight control assembly 12. The aerodynamic load simulator 30 (see FIG. 5) comprises a continuously adjustable spring rate constant assembly 40 (see FIG. 5) configured to adjust the spring rate constant 42 (see FIG. 5) of the induced simulated continuous aerodynamic load 32a (see FIG. 5) over a range of predetermined flight profiles 46a (see FIG. 5).

As further shown in FIG. 5, the aerodynamic load simulator 30 comprises an input assembly 116 configured to input a tensile load 36 and a compressive load 38 from the simulated surface 20 or the flight control surface 22 to the continuously adjustable spring rate constant assembly 40. As further shown in FIG. 5, in one embodiment, the input assembly 116 comprises crank element(s) 118, tie rod element(s) 120 and a load cell 122.

As discussed in detail above, the crank element(s) 118 (see FIG. 5) may comprise a first crank element 118a (see FIG. 1B) connected to a first tie rod 120a (see FIG. 1B) and a load cell 122 (see FIG. 1B), and may further comprise a second crank element 118b (see FIG. 1B) connected to a second tie rod 120b (see FIG. 1B). The first crank element 118a (see FIG. 1B) connected to the first tie rod 120a (see FIG. 1B) and the load cell 122 (see FIG. 1B) preferably connect the simulated surface 20 (see FIGS. 1B, 5) or the at least one flight control surface 22 (see FIG. 5) via shaft 114 (see FIG. 1B) to the beam spring 50 (see FIGS. 1B, 5) of the continuously adjustable spring rate constant assembly 40 (see FIGS. 1B, 5). The second crank element 118b (see FIG. 1B) and the second tie rod 120b (see FIG. 1B) preferably connect the simulated surface 20 (see FIGS. 1B, 5) or the at least one flight control surface 22 (see FIG. 5) via the shaft 114 (see FIG. 1B) to the test piece 24 (see FIG. 1B).

As shown in FIG. 5, the continuously adjustable spring rate constant assembly 40 comprises the beam spring 50 having the spring rate constant 42 and the spring rate 44. The spring rate 44 (see FIG. 5) preferably comprises an adjustable spring rate 44a, and more preferably comprises an automated adjustable spring rate 44b (see FIG. 5). The adjustable spring rate 44a (see FIG. 5), and more preferably, the automated adjustable spring rate 44b (see FIG. 5), is adjustable in real time and under aerodynamic load 32 (see FIG. 5) via the analog input/command signal 48 (see FIG. 5). The analog input/command signal 48 (see FIG. 5) may comprise a computer input 48a (see FIG. 5), a manual input 48b (see FIG. 5), or another suitable analog input/command signal.

As shown in FIG. 5, the continuously adjustable spring rate constant assembly 40 further comprises the base member 60, the adjustable fulcrum assembly 70, and the positioning device 100, such as in the form of sliding device 100a (see also FIG. 1E) or in the form of sliding device 100b (see also FIG. 2A), all of which are discussed in greater detail above. The adjustable fulcrum assembly 70 (see FIG. 5) is automatically positioned lengthwise along the sliding device 100a (see FIG. 5) between the first fixed end 52a (see FIGS. 1E, 2A) and the second non-fixed end 52b (see FIGS. 1E, 2A) of the beam spring 50 (see FIG. 5) to adjust the spring rate constant 42 (see FIG. 5) in real time.

As shown in FIG. 5, the continuously adjustable spring rate constant assembly 40 further comprises the support elements 108, such as in the form of hinge line trunnion elements 108a, 108b, the drive mechanism 126 with the screw element 128, and the power supply 130, such as in the form of an electric motor 130a, or another suitable power supply, all of which are also discussed in greater detail above.

Figure 6:
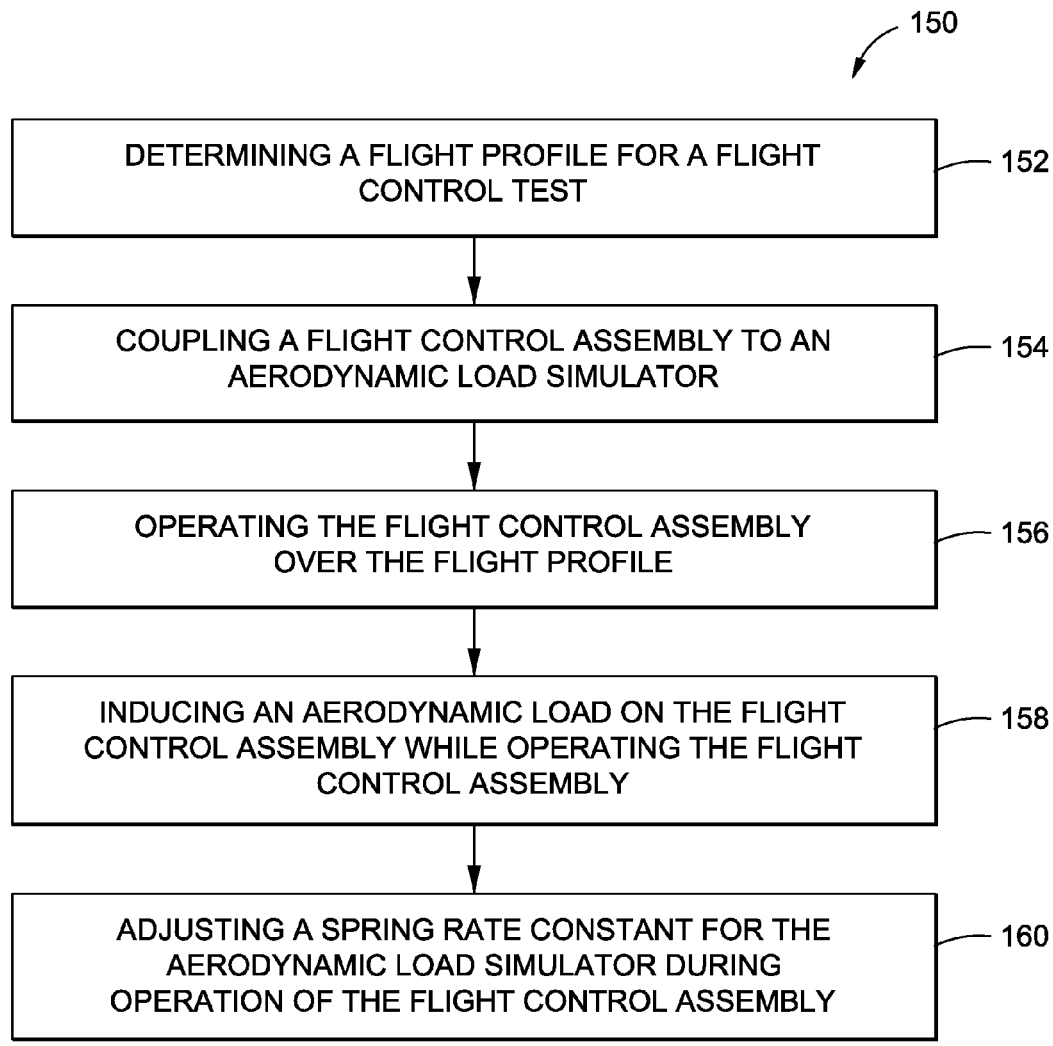
FIG. 6 is an illustration of a flow diagram of an exemplary embodiment of a method of the disclosure.

In another embodiment of the disclosure, there is provided a method 150 (see FIG. 6) for testing a simulated surface 20 (see FIGS. 1A, 5) or a flight control surface 22 (see FIG. 5). FIG. 6 is an illustration of a flow diagram of an exemplary embodiment of the method 150 of the disclosure. The method 150 is preferably automated and uses a flight control test simulator system 10 (see FIGS. 1A, 5), such as in the form of an aircraft flight control test simulator system 10a (see FIGS. 1A, 5), to perform a flight control test 25 (see FIG. 5). The flight control test simulator system 10 (see FIGS. 1A, 5) with the continuously adjustable spring rate constant assembly 40 (see FIGS. 1A, 2A, 5) provides for an automated system and method for modifying the aerodynamic load 32 (see FIG. 5) during testing, for adjusting an aerodynamic load condition 34 (see FIG. 5) during testing, and for adjusting a spring rate 44 (see FIG. 5) during testing.

As shown in FIG. 6, the method 150 comprises step 152 of determining a flight profile 46 (see FIG. 5) for a flight control test 25 (see FIG. 5). The flight profile 46 (see FIG. 5) may be determined using computations validated in a wind tunnel and obtaining flight test data that may be refined into the flight profile 46 (see FIG. 5).

As shown in FIG. 6, the method 150 further comprises step 154 of coupling a flight control assembly 12 (see FIGS. 1A, 5) to an aerodynamic load simulator 30 (see FIGS. 1A, 5). The step 154 of coupling the flight control assembly 12 (see FIGS. 1A, 5) to the aerodynamic load simulator 30 (see FIGS. 1A, 5) comprises coupling the flight control assembly 12 (see FIGS. 1A, 5) having at least one actuator 14 (see FIG. 5), such as an aircraft system actuator, and having a flight controller 16a (see FIG. 5) configured to actuate the at least one actuator 14 (see FIG. 5).

The flight control assembly 12 (see FIGS. 1A, 5) may further comprise a processing device 18 (see FIG. 5), such as a computer 18a (see FIG. 5). The processing device 18 (see FIG. 5) may be used for processing software, such as aerodynamic conditions simulation software, or other suitable software, and/or for obtaining and processing test data from the flight control test 25 (see FIG. 5) performed by the flight control test simulator system 10 (see FIG. 5).

The step 154 of coupling the flight control assembly 12 (see FIGS. 1A, 5) to the aerodynamic load simulator 30 (see FIGS. 1A, 5) preferably further comprises including a continuously adjustable spring rate constant assembly 40 (see FIGS. 1A, 5) as part of the aerodynamic load simulator 30 (see FIGS. 1A, 5). The components of the continuously adjustable spring rate constant assembly 40 (see FIGS. 1A, 5) are discussed in detail above.

As shown in FIG. 6, the method 150 further comprises step 156 of operating the flight control assembly 12 (see FIG. 1A) over the flight profile 46 (see FIG. 5).

As shown in FIG. 6, the method 150 further comprises step 158 of inducing an aerodynamic load 32 (see FIG. 5) on the flight control assembly 12 (see FIG. 1A) while operating the flight control assembly 12 (see FIG. 1A). The step 158 of inducing the aerodynamic load 32 (see FIG. 5) on the flight control assembly 12 (see FIGS. 1A, 5) preferably comprises adjustably inducing with the aerodynamic load simulator 30 (see FIGS. 1A, 5) a simulated continuous aerodynamic load 32a (see FIG. 5) on the flight control assembly 12 (see FIGS. 1A, 5). The step 158 of inducing the aerodynamic load 32 (see FIG. 5) on the flight control assembly 12 (see FIGS. 1A, 5) preferably further comprises adjusting with a continuously adjustable spring rate constant assembly 40 (see FIGS. 1A, 5) of the aerodynamic load simulator 30 (see FIGS. 1A, 5) the spring rate constant 42 (see FIG. 5) of the induced simulated continuous aerodynamic load 32a (see FIG. 5) over a range of predetermined flight profiles 46a (see FIG. 5).

The step 158 of inducing the aerodynamic load 32 (see FIG. 5) on the flight control assembly 12 (see FIGS. 1A, 5) may further comprise coupling a first crank element 118a (see FIG. 1B), a first tie rod 120a (see FIG. 1B), and a load cell 122 (see FIG. 1B) between the simulated surface 20 (see FIGS. 1B, 5) or the flight control surface 22 (see FIG. 5) and a beam spring 50 (see FIGS. 1B, 5) of the continuously adjustable spring rate constant assembly 40 (see FIGS. 1B, 5). The step 158 of inducing the aerodynamic load 32 (see FIG. 5) on the flight control assembly 12 (see FIGS. 1A, 5) may further comprise inducing a simulated continuous aerodynamic load 32a (see FIG. 5) to the beam spring 50 (see FIGS. 1B, 5) from the simulated surface 20 (see FIGS. 1B, 5) or the flight control surface 22 (see FIGS. 1B, 5) via the first crank element 118a (see FIG. 1B), the first tie rod 120a (see FIG. 1B), and the load cell 122 (see FIG. 1B).

As shown in FIG. 6, the method 150 further comprises step 160 of adjusting a spring rate constant 42 (see FIG. 5) for the aerodynamic load simulator 30 (see FIGS. 1A-1B, 5) during operation of the flight control assembly 12 (see FIGS. 1A-1B, 5). The step 160 of adjusting the spring rate constant 42 (see FIG. 5) for the aerodynamic load simulator 30 (see FIGS. 1A-1B, 5) preferably comprises coupling an adjustable fulcrum assembly 70 (see FIGS. 1A-1B, 5) to the beam spring 50 (see FIGS. 1A-1B, 5) positioned over a sliding device 100a (see FIGS. 1B, 5) that is automated. The step 160 of adjusting the spring rate constant 42 (see FIG. 5) for the aerodynamic load simulator 30 (see FIGS. 1A-1B, 5) preferably further comprises automatically positioning the adjustable fulcrum assembly 70 (see FIGS. 1A-1B, 5) lengthwise along the sliding device 100a (see FIGS. 1A-1B, 5) between a first fixed end 52a (see FIGS. 1A-1B, 5) and a second non-fixed end 52b (see FIGS. 1A-1B, 5) of the beam spring 50 (see FIGS. 1A-1B, 5) to adjust the spring rate constant 42 (see FIG. 5) in real time.

The step 160 of adjusting the spring rate constant 42 (see FIG. 5) for the aerodynamic load simulator 30 (see FIGS. 1A-1B, 5) may further comprise using a drive mechanism 126 (see FIGS. 1B, 5) to automatically position the adjustable fulcrum assembly 70 (see FIGS. 1A-1B, 5) lengthwise along the sliding device 100a (see FIGS. 1B, 5). The drive mechanism 126 (see FIGS. 1B, 5) preferably comprises a screw element 128 (see FIGS. 1B, 5) attached to the adjustable fulcrum assembly 70 (see FIGS. 1B, 5) and driven by a power supply 130 (see FIGS. 1B, 5). The power supply 130 (see FIGS. 1B, 5) may comprise an electric motor 130a or another suitable power supply.

Figure 7:
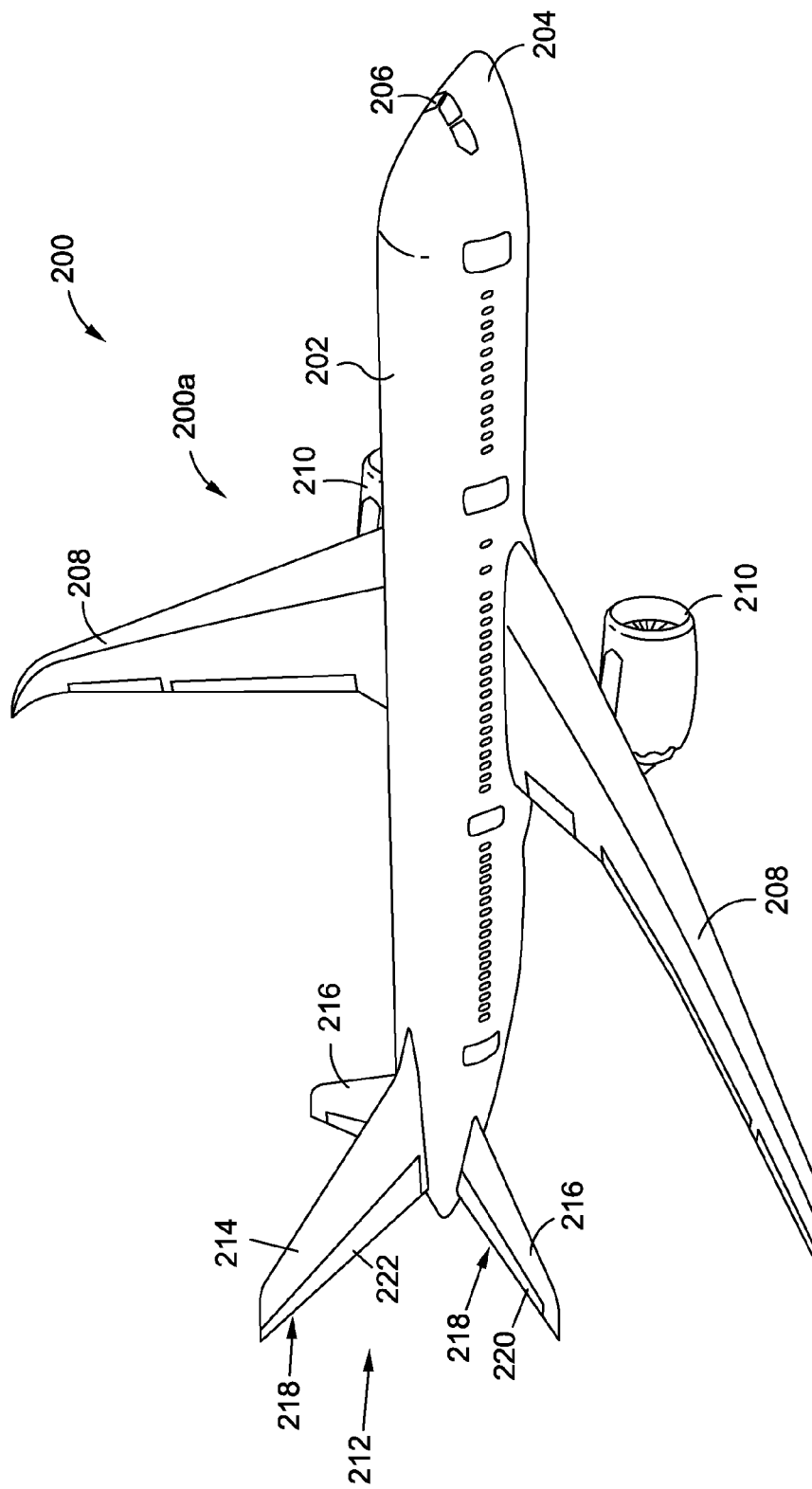
FIG. 7 is an illustration of a perspective view of an air vehicle having one or more structures that may be tested and evaluated with embodiments of a flight control test simulator system and method of the disclosure.

FIG. 7 is an illustration of a perspective view of an air vehicle 200, such as an aircraft 200a, having one or more structures 218, such as in the form of an elevator component 220 or a rudder component 222, that may be tested and evaluated with embodiments of the flight control test simulator system 10 (see FIG. 1A) and the method 150 (see FIG. 6) of the disclosure, as discussed in detail above. As shown in FIG. 7, the air vehicle 200, such as in the form of aircraft 200a, comprises a fuselage 202, a nose 204, a cockpit 206, wings 208, one or more propulsion units 210, and a tail 212 comprising a vertical tail portion 214 and horizontal tail portions 216.

Although the aircraft 200a shown in FIG. 7 is generally representative of a commercial passenger aircraft having one or more structures 218, such as in the form of the elevator component 220 or the rudder component 222, the teachings of the disclosed embodiments may be applied to other passenger aircraft. For example, the teachings of the disclosed embodiments may be applied to cargo aircraft, military aircraft, rotorcraft, and other types of aircraft or aerial vehicles, as well as aerospace vehicles, satellites, space launch vehicles, rockets, and other aerospace vehicles.

Figure 8:
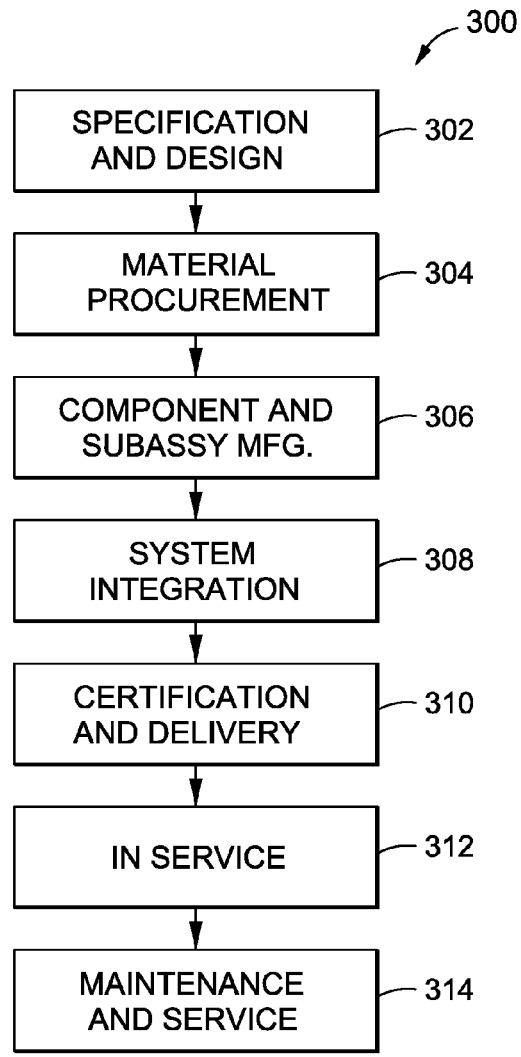
FIG. 8 is an illustration of a flow diagram of an aircraft manufacturing and service method; and, FIG. 9 is an illustration of a functional block diagram of an embodiment of an aircraft of the disclosure.
Figure 9:
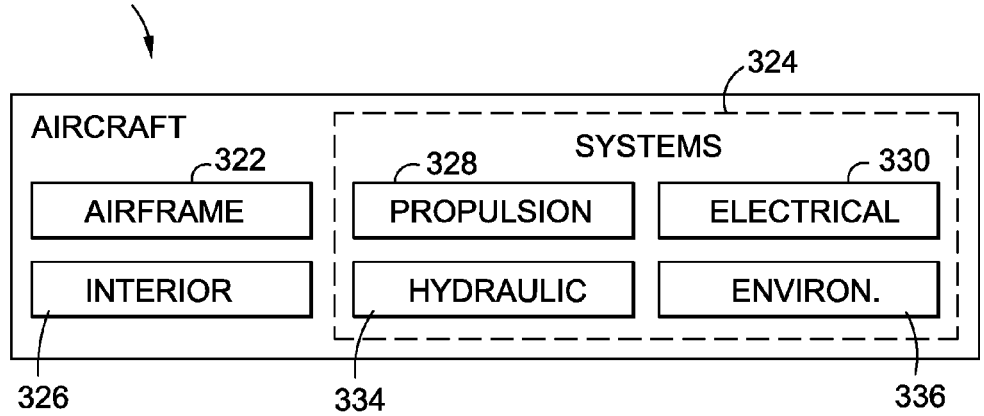

FIG. 8 is an illustration of a flow diagram of an aircraft manufacturing and service method 300. FIG. 9 is an illustration of a functional block diagram of an embodiment of an aircraft 320 of the disclosure. Referring to FIGS. 8-9, embodiments of the disclosure may be described in the context of the aircraft manufacturing and service method 300 as shown in FIG. 8, and the aircraft 320 as shown in FIG. 9.

During pre-production, exemplary aircraft manufacturing and service method 300 may include specification and design 302 of the aircraft 320 and material procurement 304. During manufacturing, component and subassembly manufacturing 306 and system integration 308 of the aircraft 320 takes place. Thereafter, the aircraft 320 may go through certification and delivery 310 in order to be placed in service 312. While in service 312 by a customer, the aircraft 320 may be scheduled for routine maintenance and service 314 (which may also include modification, reconfiguration, refurbishment, and other suitable services).

Each of the processes of the aircraft manufacturing and service method 300 may be performed or carried out by a system integrator, a third party, and/or an operator (e.g., a customer). For the purposes of this description, a system integrator may include, without limitation, any number of aircraft manufacturers and major-system subcontractors. A third party may include, without limitation, any number of vendors, subcontractors, and suppliers. An operator may include an airline, leasing company, military entity, service organization, and other suitable operators.

As shown in FIG. 9, the aircraft 320 produced by the exemplary aircraft manufacturing and service method 300 may include an airframe 322 with a plurality of systems 324 and an interior 326. Examples of the plurality of systems 324 may include one or more of a propulsion system 328, an electrical system 330, a hydraulic system 332, and an environmental system 334. Any number of other systems may be included. Although an aerospace example is shown, the principles of the disclosure may be applied to other industries, such as the automotive industry.

Methods and systems embodied herein may be employed during any one or more of the stages of the aircraft manufacturing and service method 300. For example, components or subassemblies corresponding to component and subassembly manufacturing 306 may be fabricated or manufactured in a manner similar to components or subassemblies produced while the aircraft 320 is in service 312. Also, one or more apparatus embodiments, method embodiments, or a combination thereof, may be utilized during component and subassembly manufacturing 306 and system integration 308, for example, by substantially expediting assembly of or reducing the cost of the aircraft 320. Similarly, one or more of apparatus embodiments, method embodiments, or a combination thereof, may be utilized while the aircraft 320 is in service 312, for example and without limitation, to maintenance and service 314.

Disclosed embodiments of the flight control test simulator system 10 (see FIGS. 1A, 5) and method 150 (see FIG. 6) provide a continuously adjustable spring rate constant assembly 40 (see FIGS. 1A, 5) with a beam spring 50 (see FIG. 1B) having an adjustable spring rate 44a (see FIG. 5). The beam spring 50 (see FIG. 1B) has an automated, adjustable spring rate 44 (see FIG. 5) for simulating aerodynamic loads 32 (see FIG. 5) to obtain simulated continuous aerodynamic loads 32a (see FIG. 5). In addition, disclosed embodiments of the flight control test simulator system 10 (see FIGS. 1A, 5) and method 150 (see FIG. 6) provide an input assembly 116 (see FIGS. 1A-1C), including a first crank element 118a (see FIGS. 1A-1C), a first tie rod 120a (see FIGS. 1A-1C) and a load cell 122 (see FIGS. 1B-1C), that inputs aerodynamic load 32 (see FIG. 5) or force from a simulated surface 20 (see FIGS. 1A, 5) or a flight control surface 22 (see FIG. 5) to a beam spring 50 (see FIGS. 1A, 5), and that provide an adjustable fulcrum assembly 70 (see FIGS. 1A, 5) that moves in an automated fashion.

The flight control test simulator system 10 (see FIGS. 1A, 5) and method 150 (see FIG. 6) with the continuously adjustable spring rate constant assembly 40 (see FIGS. 1A, 2A, 5) provide an automated system and method for modifying the aerodynamic load 32 (see FIG. 5) during testing, for adjusting the aerodynamic load condition 34 (see FIG. 5) during testing, and for adjusting a spring rate 44 (see FIG. 5) during testing. The spring rate 44 (see FIG. 5) may be adjusted or modified during testing in real time, under load, by means of an analog input/command signal 48 (see FIG. 5). In addition, no tools are required to adjust the spring rate 44 (see FIG. 5).

Disclosed embodiments of the flight control test simulator system 10 (see FIGS. 1A, 5) and method 150 (see FIG. 6) enable testing to be performed on test pieces 24 (see FIG. 1A), such as in the form of aircraft test pieces 24a (see FIG. 1A), at a higher test rate than testing using certain existing test systems and methods. This is due to the elimination of test downtime, the elimination of labor to adjust spring rates 44 (see FIG. 5), the simplification of test planning, and the ability to execute more realistic test scenarios.

Disclosed embodiments of the flight control test simulator system 10 (see FIGS. 1A, 5) and method 150 (see FIG. 6) may be advantageous over existing active systems and methods in that they are more cost effective, more repeatable, and simpler. Further, disclosed embodiments of the flight control test simulator system 10 (see FIGS. 1A, 5) and method 150 (see FIG. 6) may be advantageous over existing passive systems and methods in that the testing does not need to be stopped and may be less costly due to minimization or elimination of labor to adjust spring rates 44 (see FIG. 5), due to increased testing efficiency, and due to increased accuracy of testing.

Many modifications and other embodiments of the disclosure will come to mind to one skilled in the art to which this disclosure pertains having the benefit of the teachings presented in the foregoing descriptions and the associated drawings. The embodiments described herein are meant to be illustrative and are not intended to be limiting or exhaustive. Although specific terms are employed herein, they are used in a generic and descriptive sense only and not for purposes of limitation.

What is claimed is:

1. A flight control test simulator system, the system comprising:
   a flight control assembly having at least one actuator and having a flight controller configured to actuate the at least one actuator; and
   an aerodynamic load simulator coupled to the flight control assembly and configured to adjustably induce a simulated continuous aerodynamic load on the flight control assembly, the aerodynamic load simulator having a continuously adjustable spring rate constant assembly configured to adjust the spring rate constant of the induced simulated continuous aerodynamic load over a range of predetermined flight profiles.

2. The system of claim 1 wherein the flight control assembly further comprises a simulated surface or at least one flight control surface.

3. The system of claim 2 wherein the simulated surface comprises a rotating flywheel or a flight control inertia mass simulator.

4. The system of claim 2 wherein the aerodynamic load simulator comprises an input assembly configured to input a tensile load and a compressive load from the simulated surface to the continuously adjustable spring rate constant assembly.

5. The system of claim 4 wherein the input assembly comprises a first crank element connected to a first tie rod and a load cell, and wherein the first crank element, the first tie rod and the load cell connect the simulated surface via a shaft to a beam spring.

6. The system of claim 5 wherein the input assembly further comprises a second crank element connected to a second tie rod, and wherein the second crank element and the second tie rod connect the simulated surface via the shaft to a test piece.

7. The system of claim 1 wherein the continuously adjustable spring rate constant assembly comprises:
   a base member;
   a positioning device attached to the base member;
   a beam spring having a first fixed end attached to a first end of the base member and having a second non-fixed end, the beam spring positioned over the positioning device;
   an adjustable fulcrum assembly coupled to the beam spring and configured to move lengthwise along the positioning device between the first fixed end and the second non-fixed end of the beam spring to create contact between the beam spring and the base member;
   a drive mechanism configured to move the adjustable fulcrum assembly lengthwise along the positioning device; and
   at least two support elements connected to the base member.

8. The system of claim 7 wherein the positioning device comprises a sliding device that is automated.

9. The system of claim 7 wherein the drive mechanism comprises a screw element attached to the adjustable fulcrum assembly, the screw element being driven by a power supply.

10. The system of claim 7 wherein the beam spring has an adjustable spring rate that is adjustable in real time and under aerodynamic load by an analog input/command signal.

11. An aircraft flight control test simulator system for testing a simulated surface or a flight control surface, the aircraft flight control test simulator system being automated and comprising:
   a flight control assembly having at least one actuator, having a flight controller configured to actuate the at least one actuator, and having the simulated surface or the flight control surface; and,
   an aerodynamic load simulator coupled to the flight control assembly and configured to adjustably induce a simulated continuous aerodynamic load on the flight control assembly, the aerodynamic load simulator comprising:
      a continuously adjustable spring rate constant assembly configured to adjust the spring rate constant of the induced simulated continuous aerodynamic load over a range of predetermined flight profiles; and
      an input assembly configured to input a tensile load and a compressive load from the simulated surface or the flight control surface to the continuously adjustable spring rate constant assembly.

12. The system of claim 11 wherein the continuously adjustable spring rate constant assembly comprises:
   a base member;
   a sliding device that is automated and attached to the base member;
   a beam spring having a first fixed end attached to a first end of the base member and having a second non-fixed end, the beam spring positioned over the sliding device;
   an adjustable fulcrum assembly coupled to the beam spring and configured to move lengthwise along the sliding device between the first fixed end and the second non-fixed end of the beam spring to create contact between the beam spring and the base member;
   a drive mechanism configured to move the adjustable fulcrum assembly lengthwise along the sliding device; and
   at least two support elements connected to the base member.

13. The system of claim 12 wherein the adjustable fulcrum assembly is automatically positioned lengthwise along the sliding device between the first fixed end and the second non-fixed end of the beam spring to adjust the spring rate constant in real time.

14. The system of claim 11 wherein the input assembly comprises a first crank element connected to a first tie rod and a load cell, and further comprises a second crank element connected to a second tie rod, and wherein the first crank element connected to the first tie rod and the load cell connect the simulated surface or the flight control surface via a shaft to a beam spring of the continuously adjustable spring rate constant assembly, and further wherein the second crank element and the second tie rod connect the simulated surface or the flight control surface via the shaft to a test piece.

15. A method for testing a simulated surface or a flight control surface, the method comprising the steps of:
   determining a flight profile for a flight control test;
   coupling a flight control assembly to an aerodynamic load simulator;
   operating the flight control assembly over the flight profile;
   inducing an aerodynamic load on the flight control assembly while operating the flight control assembly; and,
   adjusting a spring rate constant for the aerodynamic load simulator during operation of the flight control assembly.

16. The method of claim 15 wherein the step of coupling the flight control assembly to the aerodynamic load simulator comprises coupling the flight control assembly having at least one actuator and having a flight controller configured to actuate the at least one actuator.

17. The method of claim 15 wherein the step of inducing the aerodynamic load on the flight control assembly comprises adjustably inducing with the aerodynamic load simulator a simulated continuous aerodynamic load on the flight control assembly, and adjusting with a continuously adjustable spring rate constant assembly of the aerodynamic load simulator the spring rate constant of the induced simulated continuous aerodynamic load over a range of predetermined flight profiles.

18. The method of claim 15 wherein the step of inducing the aerodynamic load on the flight control assembly comprises coupling a first crank element, a first tie rod, and a load cell between the simulated surface or the flight control surface and a beam spring of a continuously adjustable spring rate constant assembly of the aerodynamic load simulator, and inducing a simulated continuous aerodynamic load to the beam spring from the simulated surface or the flight control surface via the first crank element, the first tie rod, and the load cell.

19. The method of claim 15 wherein the step of adjusting the spring rate constant for the aerodynamic load simulator comprises coupling an adjustable fulcrum assembly to a beam spring positioned over a sliding device that is automated, and automatically positioning the adjustable fulcrum assembly lengthwise along the sliding device between a first fixed end and a second non-fixed end of the beam spring to adjust the spring rate constant in real time.

20. The method of claim 19 wherein the step of adjusting the spring rate constant for the aerodynamic load simulator further comprises using a drive mechanism to automatically position the adjustable fulcrum assembly lengthwise along the sliding device, wherein the drive mechanism comprises a screw element attached to the adjustable fulcrum assembly and driven by a power supply.

* * * * *